United States Patent [19]
White

[11] Patent Number: 5,764,874
[45] Date of Patent: *Jun. 9, 1998

[54] IMAGING SYSTEM UTILIZING BOTH DIFFUSE AND SPECULAR REFLECTION CHARACTERISTICS

[75] Inventor: Timothy Peter White, New Boston, N.H.

[73] Assignee: Northeast Robotics, Inc., Weare, N.H.

[*] Notice: The term of this patent shall not extend beyond the expiration date of Pat. No. 5,604,550.

[21] Appl. No.: 725,189

[22] Filed: Oct. 8, 1996

Related U.S. Application Data

[63] Continuation-in-part of Ser. No. 501,213, Jul. 11, 1995, Pat. No. 5,604,550, which is a continuation-in-part of Ser. No. 331,882, Oct. 31, 1994, Pat. No. 5,539,485.

[51] Int. Cl.⁶ .................................................. G03B 15/03
[52] U.S. Cl. ........................ 396/155; 396/200; 396/429; 362/16; 355/67
[58] Field of Search ................................. 396/429, 1, 4, 396/155, 200; 355/67, 70, 71; 362/4, 89, 3, 16

[56] References Cited

U.S. PATENT DOCUMENTS

| | | |
|---|---|---|
| 2,792,740 | 5/1957 | Haynes . |
| 2,926,559 | 3/1960 | Oppenheimer . |
| 2,934,601 | 4/1960 | Oppenheimer . |
| 3,322,487 | 5/1967 | Renner . |
| 3,558,894 | 1/1971 | Odone et al. . |
| 3,596,083 | 7/1971 | Lovering . |
| 3,944,336 | 3/1976 | Carr, Jr. . |
| 3,984,157 | 10/1976 | LeVantine . |
| 3,985,425 | 10/1976 | Clapp . |
| 4,067,026 | 1/1978 | Pappanikolaou . |
| 4,139,306 | 2/1979 | Norton . |
| 4,185,902 | 1/1980 | Plaot . |
| 4,341,449 | 7/1982 | Iwata et al. . |
| 4,555,635 | 11/1985 | Yoshida . |
| 4,561,722 | 12/1985 | Smetana . |
| 4,601,576 | 7/1986 | Galbraith . |
| 4,677,473 | 6/1987 | Okamoto et al. . |
| 4,691,231 | 9/1987 | Fitzmorris et al. . |
| 4,712,889 | 12/1987 | Schindl . |
| 4,791,534 | 12/1988 | Lindberg . |
| 4,816,686 | 3/1989 | Hara et al. . |
| 4,854,688 | 8/1989 | Hayford et al. . |
| 4,877,326 | 10/1989 | Chadwick et al. . |
| 4,882,498 | 11/1989 | Cochran et al. . |
| 4,965,665 | 10/1990 | Amir . |
| 4,972,093 | 11/1990 | Cochran et al. . |
| 4,991,947 | 2/1991 | Sander et al. . |
| 5,011,265 | 4/1991 | Tamamura et al. . |
| 5,039,868 | 8/1991 | Kobayashi et al. . |
| 5,051,825 | 9/1991 | Cochran et al. . |
| 5,060,065 | 10/1991 | Wasserman . |
| 5,064,291 | 11/1991 | Reiser . |
| 5,072,127 | 12/1991 | Cochran et al. . |
| 5,155,558 | 10/1992 | Tannenbaum et al. . |
| 5,172,005 | 12/1992 | Cochran et al. . |
| 5,187,611 | 2/1993 | White et al. . |
| 5,461,417 | 10/1995 | White et al. . |
| 5,604,550 | 2/1997 | White ................................ 396/429 |

*Primary Examiner*—David M. Gray
*Attorney, Agent, or Firm*—Davis and Bujold

[57] ABSTRACT

An imaging system incorporating an illumination device, for illuminating an object to be observed with a continuous diffuse wide angle light source which is supplied along an observation axis of the imaging system, and an observation device is position along the observation axis for observing a reflection of the object to be observed. The illumination device and the observation device are both spaced a sufficient distance from the object to be observed so that the reflection of specular areas of the object can be perceived at an intensity which is substantially equal to the intensity of the continuous diffuse light supplied along the observation axis while the reflection of diffuse areas of the object can be perceived at an intensity substantially less than the intensity of the continuous diffuse light supplied along the observation axis, due to scattering of the supplied continuous diffuse light by diffuse areas upon reflection, so that the observation device can readily determine, due to the differences in the reflected intensities of the supplied light, at least one of the shape, the orientation, the boundary, the boarder, etc. between such areas and utilize that information for controlling a desired associated production operation or function.

18 Claims, 13 Drawing Sheets

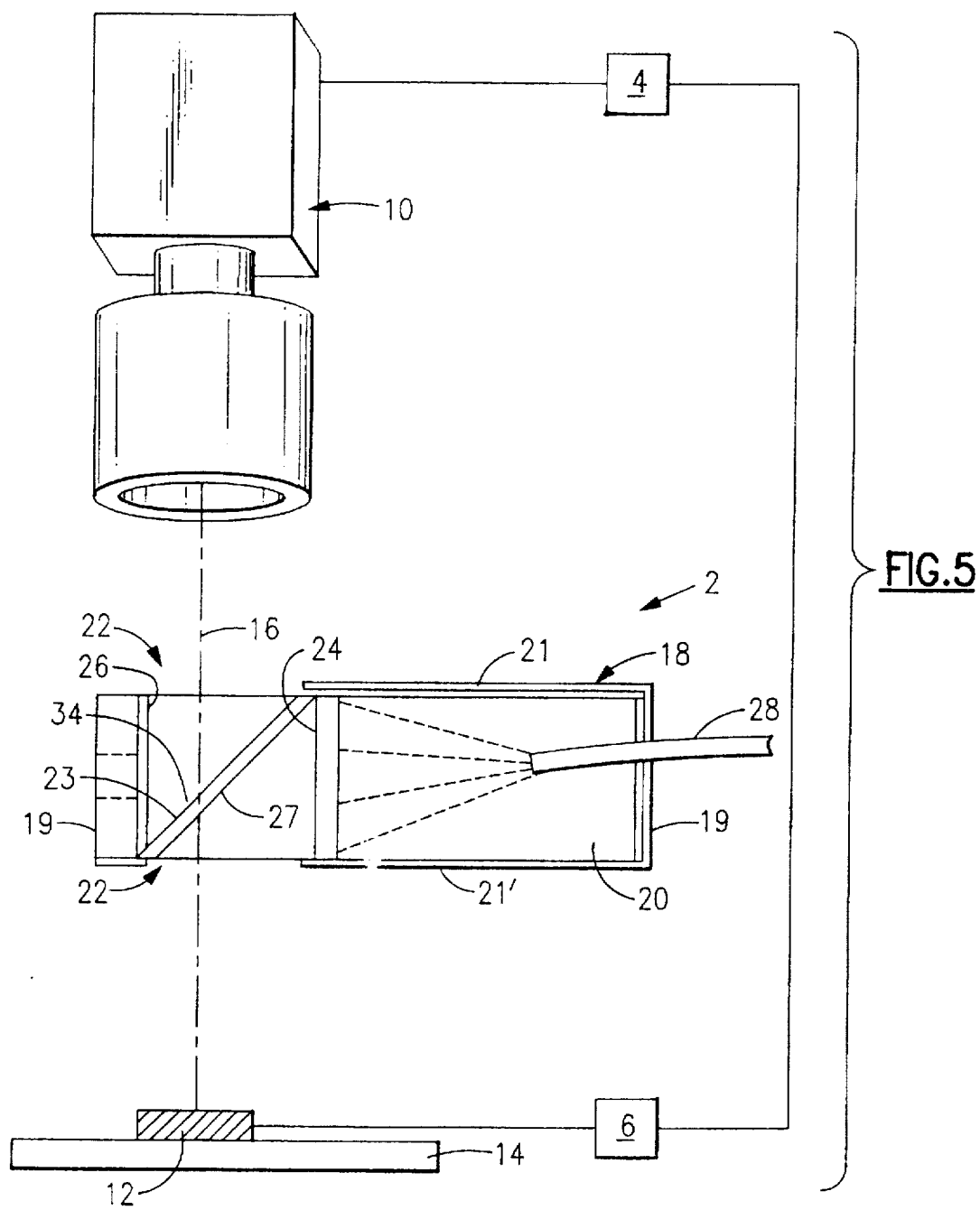

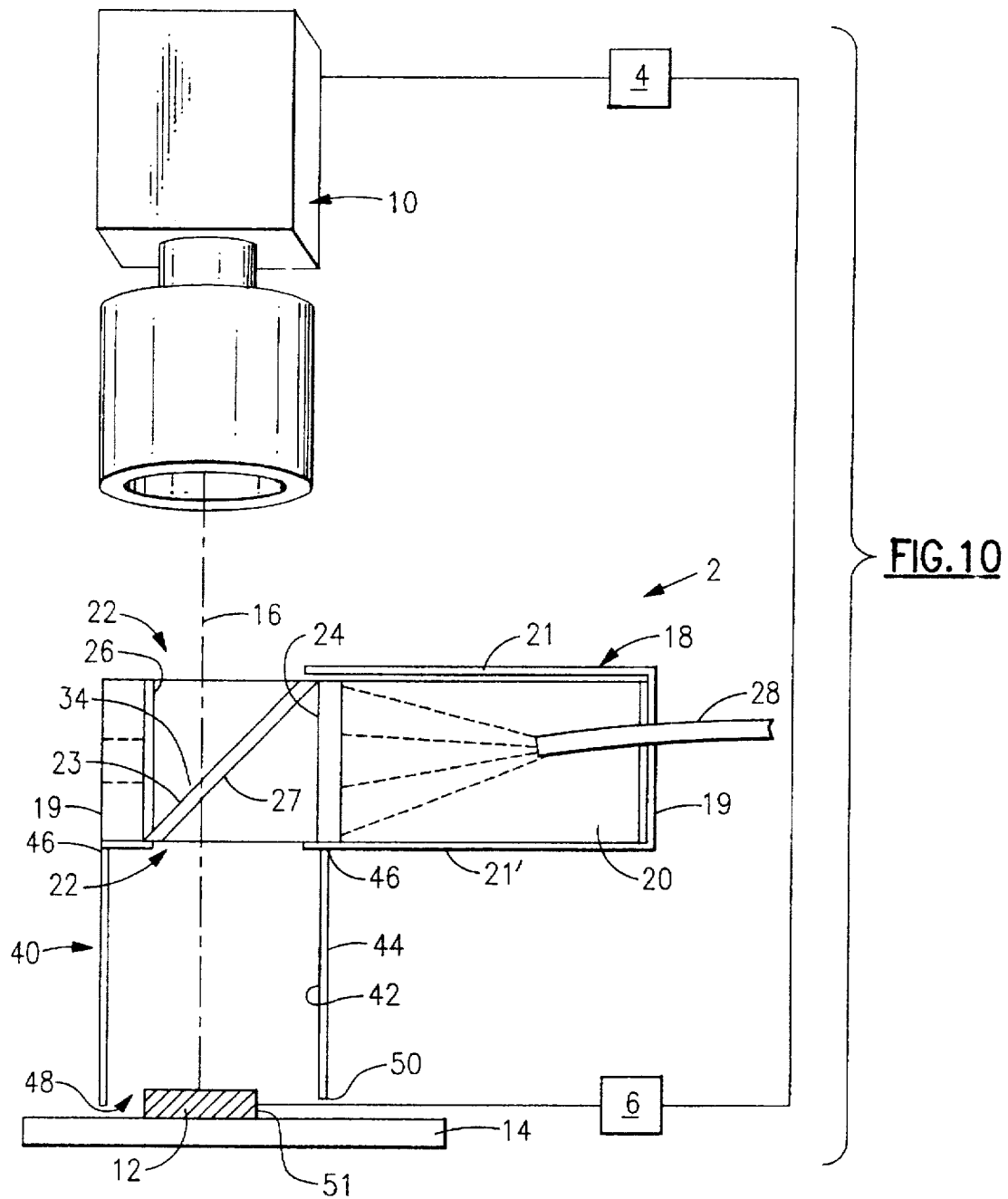

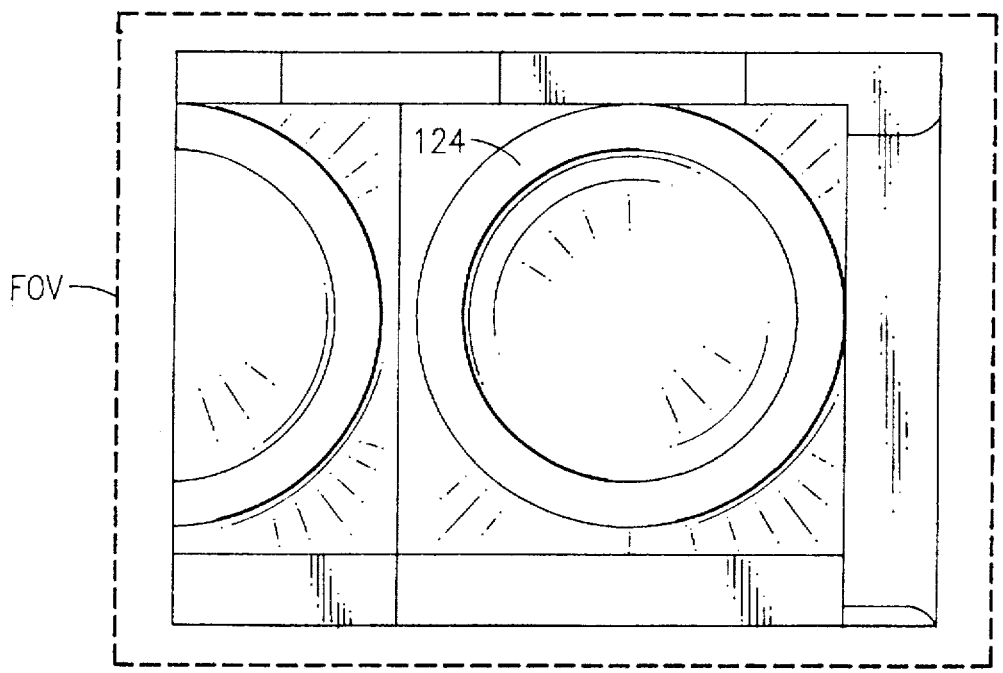
FIG.15B
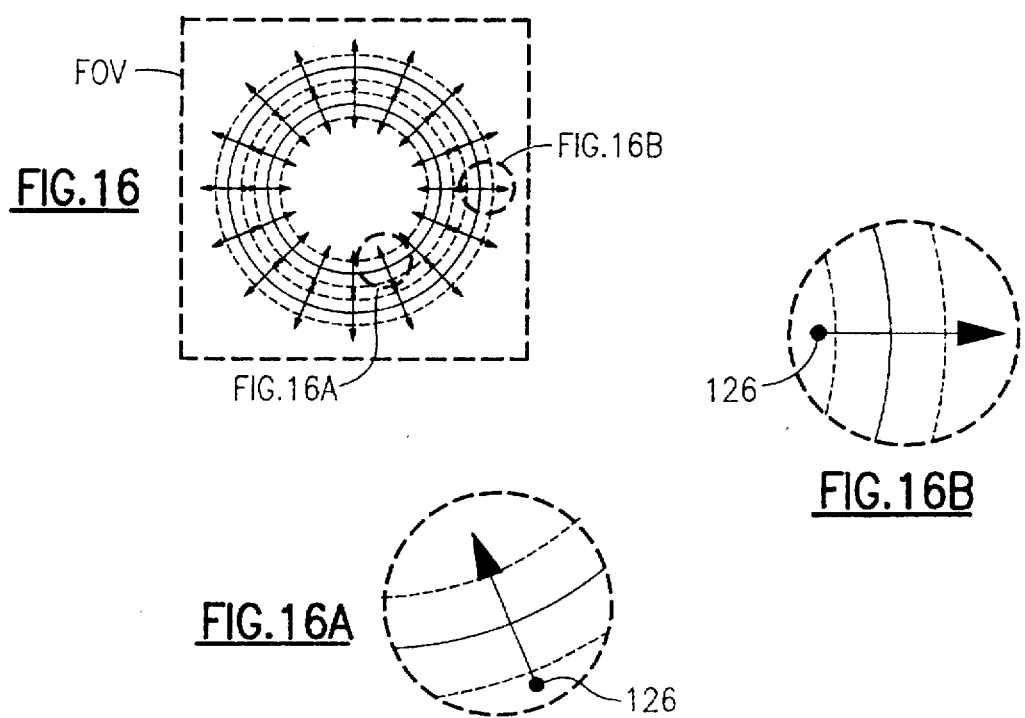
FIG.16
FIG.16A
FIG.16B

IMAGING SYSTEM UTILIZING BOTH DIFFUSE AND SPECULAR REFLECTION CHARACTERISTICS

This is a Continuation-In-Part of application Ser. No. 08/501,213 filed Jul. 11, 1995, now U.S. Pat. No. 5,604,550 which is a Continuation-In-Part of application Ser. No. 08/331,882 filed Oct. 31, 1994, now U.S. Pat. No. 5,539,485.

FIELD OF THE INVENTION

This invention pertains to an imaging system for illuminating an object to be observed, by a machine vision camera or the like for example, with a continuous diffuse wide angle light whose illumination is supplied along the observation axis and the observation device or machine vision camera is located along the observation axis and is spaced a desired distance from the object to be observed so that the areas of the object, with a relatively high specular value, reflect the supplied light more efficiently than the areas of the object, with a relatively low specular value, which scatter (diffuse) the light in a plurality of different directions, including reflecting some light back along the observation axis. The machine vision camera is able to readily discern the difference in reflection intensities, between the shiny specular areas and the diffuse areas, to determine the shape, orientation, boundary, border, etc. between the specular and diffuse areas.

BACKGROUND OF THE INVENTION

Robotics assembly machines often utilize video cameras to observe a component, part or work piece being handled, machined or assembled. For instance, in the assembly of electronic components, the chips or wafers are often assembled into printed circuit boards by robots utilizing video cameras to position the components and/or to inspect the assembled device for defects throughout the process.

In the microelectronics industry, solder pads on surface-mount devices are often observed by machine vision systems for assembly and manufacturing purposes. The accuracy and reliability of a machine vision system is critical for proper alignment of the numerous components which are to be mounted on a printed circuit board. For optimum alignment, solder pads must be clearly observed in high contrast with their background.

Components in many industries often utilize etched characters appearing on mirror like surfaces that serve to identify the components and to accurately position them during assembly. In order to permit a clear image of the characters to be produced in the camera for accurate inspection or manipulation of the parts by the robotics handling equipment, it is important that the observed object be properly illuminated.

Proper illumination of many different shiny and uneven surfaces, e.g. solder connections, foil packaging, ball bearings, etc., is critical if high quality robotics assembly is to be achieved. However, such shiny and uneven surfaces are difficult to illuminate for accurate video imaging, and this creates a need for improved illumination of such objects being observed by machine vision cameras.

When using previously available illumination systems to illuminate work pieces having uneven, highly reflective surfaces, the uneven reflection of light from these surfaces frequently produces erroneous images and signals when viewed through the camera thereby possibly resulting in an erroneous signal or incorrect/inaccurate measurement. Errors of one or two thousands of an inch in a fiducial location measurement for a single component are sufficient to ruin a large and expensive circuit board. Furthermore, previously available illumination systems for robotics handling of items have not produced a light which is uniform over the entire object being observed. As a result, the reflected image suffers from erroneous shadows, glints and glare thereby rendering it difficult to determine the precise location, quality or other characteristic(s) of the object.

To date, many illumination devices have been developed to provide substantially uniform illumination of an object to be viewed, but such known illumination devices are fairly large and cumbersome and are thus difficult to integrate into an electronic manufacturing process. For example, one of the Inventor's known light system might occupy a volume of 300 cubic inches and weigh several pounds, thereby adding to the costs and expense in constructing machine vision equipment in a very competitive industry. It is desirable to manufacture a miniature illumination device which may occupy 8 cubic inches or less and only weigh a few ounces. Such miniaturization allows significant cost savings and lessens the expense of the machinery for inspecting manufactured products.

It has been particularly problematic to view or inspect components or products which have both shiny specular reflection areas and diffuse reflection areas. Such a difference in reflection characteristics can be brought about by the object being inspected having two different components, substances or materials which have very different reflection characteristics. For example, in the case of inspecting a plastic laminate on a paper substrate, the plastic laminate has very high specular reflection characteristics while the paper has diffuse (lower specular) reflection characteristics. There are a variety of applications where a product has both specular and diffuse reflection areas and it would be beneficial to be able to view those two areas accurately to determine the relative location of the specular areas with respect to the diffuse areas to ensure that proper lamination, positioning, packaging, etc. of the object or component has occurred.

One problem which occurs with some prior art inspection devices is that sometimes less than a 100 percent of the surface being imaged and located within the region of interest ROI reflects light back along the observation axis to the observation device. In such instances, the lack or absence of light being reflected by a portion of the surface of interest does not indicate to the observation device whether there is a hole in the object being observed, e.g. the light is passing therethrough, or whether all of the supplied light is being reflected by the surface, due to its surface geometry, away from the observation device, i.e. no light is reflected back along the observation axis to the observation device.

SUMMARY OF THE INVENTION

Wherefore it is an object of the invention to overcome the above noted drawbacks of the prior art illumination devices.

It is another object of the present invention to develop an improved continuous diffuse illumination device for machine vision systems having a simplistic design which precisely determines the location, shape, boundary, relative position, etc. of the object or objects being observed.

It is a further object of the invention to develop an diffuse wide angle illumination field to improve image quality and to determine accurately a boarder or boundary between a specular area and a diffuse area of an object or objects, such as found in the electronic and pharmaceutical manufacturing processes, e.g. circuit boards, components, prepackaged pills, prepackaged capsules, and other similar items.

Another object of the invention is to supply collimated light to an object to be observed and to reflect the supplied collimated light back to an observation device with the observation device being positioned at a sufficient distance such that the different reflected characteristics of the supplied light can be readily perceived by the observation device.

Yet another object of the invention is to position the observation device at a sufficient distance from the object to be observed such that the intensity of the reflected light from a diffused area is of a sufficiently less intensity than the intensity of light reflected from a specular area so that detection of borders, boundaries or other characteristics between the specular and diffuse areas can be readily discerned.

A still further object of the invention is to facilitate detection of a substance on a flat surface to be able to detect the location of the substance and/or determine whether or not the substance is properly applied to and locate on the surface. This accomplished by spacing the imaging device, from the surface to be observed, a sufficient distant so as to be able to distinguish the relative flux of two intermingled reflected light fields of different character from one another, i.e. one light field which retains its intensity as the reflected light travels along the observation axis and approaches the observation device and a second light field whose intensity diminishes the further the reflected light travels along the observation axis and approaches the observation device.

Yet another object of the present invention is to supply a continuous diffuse light to the object to be observed and to space or arrange the observation device at a sufficient distance from the object to be observed such that the observation device senses 100 percent of the surface area to be observed and located within the region of interest so that at least one characteristic of 100 percent of the surface area being observed can be discerned to determine whether holes or other abnormalities exist within the object to be observed.

These and other objects of the invention are realized by (insert claim 1 here).

The invention also relates to a (insert claim 14 here).

The invention also relates to (insert claim 16 here).

BRIEF DESCRIPTION OF THE DRAWINGS

The invention will now be described, by way of example, with reference to the attached drawings, in which:

FIG. 5 is a diagrammatic illustration of an continuous diffuse illumination device, equipped with an inspection camera and other associated equipment, providing light along the observation axis;

FIG. 10 is a diagrammatic illustration of a modification of the continuous diffuse illumination device of FIG. 5 incorporating a light barrier;

FIG. 15B shows an image of a seal, from a foil side of a packaging material, using the illumination techniques of the present invention which essentially eliminates the art work; and FIG. 16, FIG. 16A and FIG. 16B diagrammatically shows a process for detection of the location of the seal area according to the techniques of the present invention.

DESCRIPTION OF THE PREFERRED EMBODIMENTS

Prior to discussing the present invention in detail, a brief discussion concerning the lighting technology of the present invention will first be provided.

To date, when a machine vision lighting person is typically given a particular lighting application to solve, such lighting person will generally subject the object to be illuminated to various lighting angles, light conditions, etc. However, there are certain basis rules that are observed by the lighting person. The first is when employing a continuous diffused illuminator, such as a unit sold by Northeast Robotics, Inc. of Weare, N.H. under the trademark DOAL®, the continuous diffused illumination device is generally placed relatively close to the object, e.g. within 1–2 inches of the object.

Figure 1:
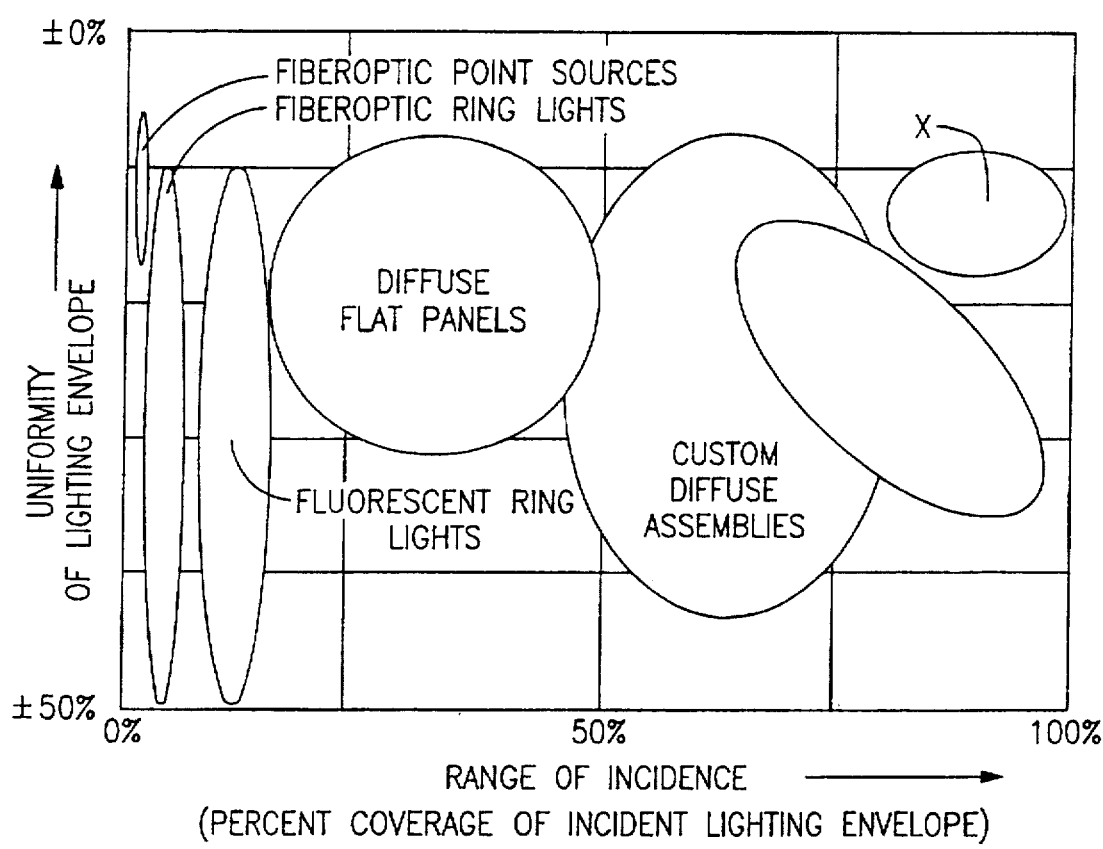
FIG. 1 is a graph depicting the characteristics of "diffuse" light.

The term "diffuse", as used in this specification and the appended claims and when referring to a light source, means a light source which is uniformly dispersed over a broad range of incident angle of azimuth and elevation with respect to the object being observed, and the light source approaches complete coverage over the area where the light is directed, i.e. greater than 80% of the possible angular range of incident light-approaching area X labelled in FIG. 1.

The term "specular reflection", as used in this specification and the appended claims, means a reflection of light by a portion or area of an object to be observed, back along the observation axis, at substantially the same intensity as the intensity of the supplied light.

The term "diffuse reflection", as used in this specification and the appended claims, means a reflection light by a portion or area of an object to be observed, back along the observation axis, at a substantially less intensity than the intensity of the supplied light whereby only a portion of the supplied light is reflected back along the observation axis.

Figure 2:
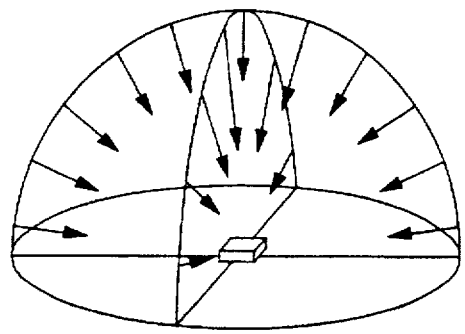
FIG. 2 is a diagrammatic representation of a desired hemispheric lighting envelope.

Turning now to FIG. 1, this figure is a graph depicting the characteristics of a diffuse light source while FIG. 2 depicts a lighting envelope which has uniformity over a complete range of incidence of the lighting envelope which is particularly adapted to determine the appearance of specular (shiny) objects and surfaces. Variations in the appearance of the specular objects and surfaces are minimized by having a continuous unbroken field of illumination and a maximum uniformity of the incident light.

The present inventor has appreciated that there are two basic reflection characteristics for light, namely, a specular reflection characteristic and a diffused reflection characteristic. It was noted by the present inventor that a variety of different materials, liquids, substances, constituents, etc. will provide a specular reflection while a variety of other items will provide a diffuse reflection, e.g. paper.

Figure 3:
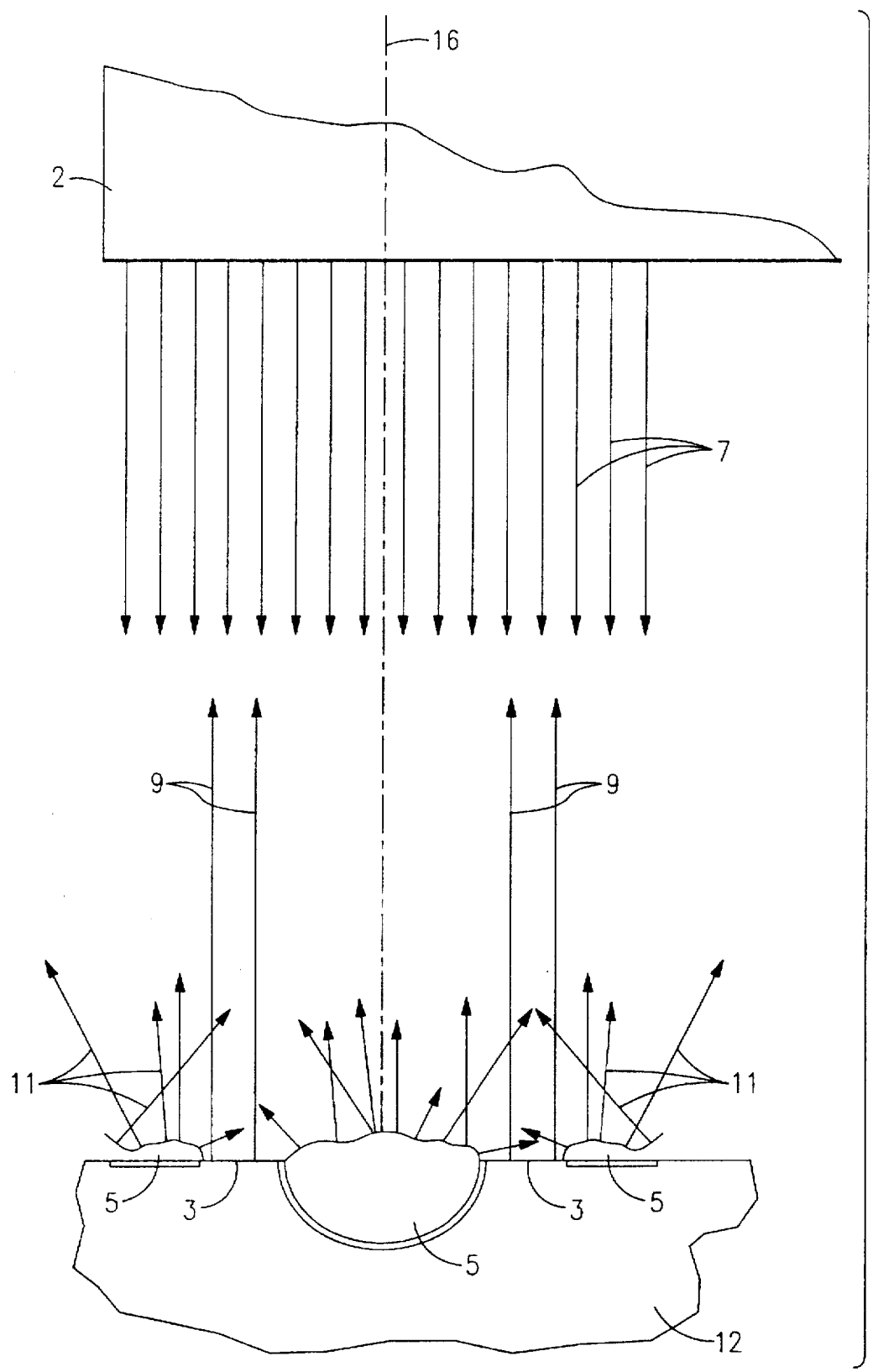
FIG. 3 is a diagrammatic representation showing the supply of collimated light to an object having both diffuse and specular reflective characteristics.
Figure 4A:
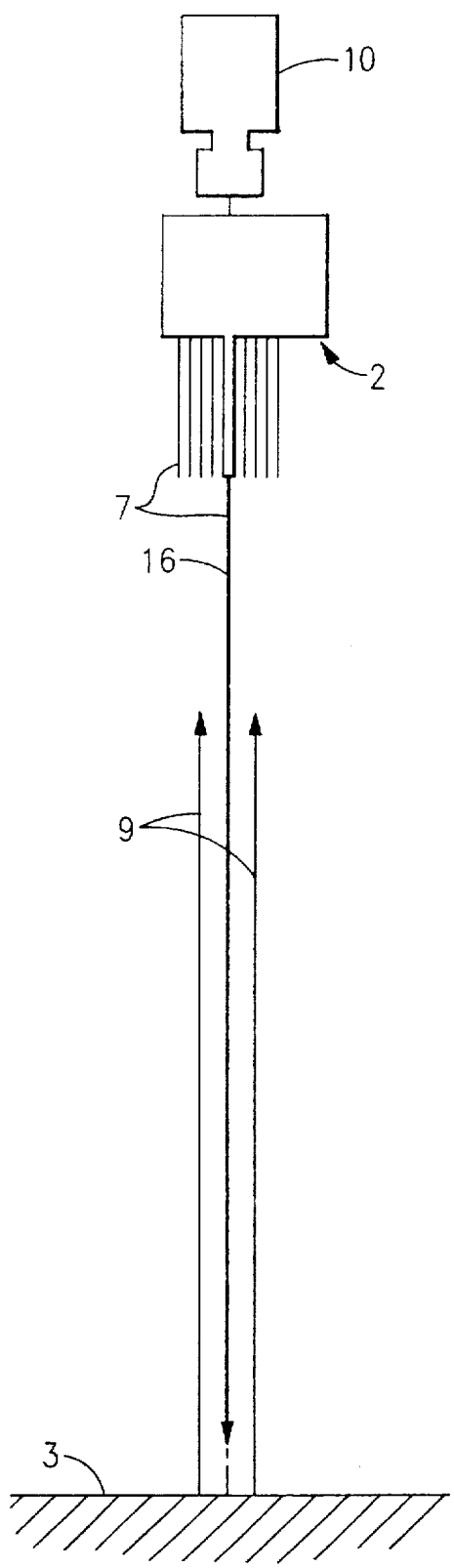
FIG. 4A diagrammatically shows the reflection by an object of the collimated light supplied to a specular reflection area.
Figure 4B:
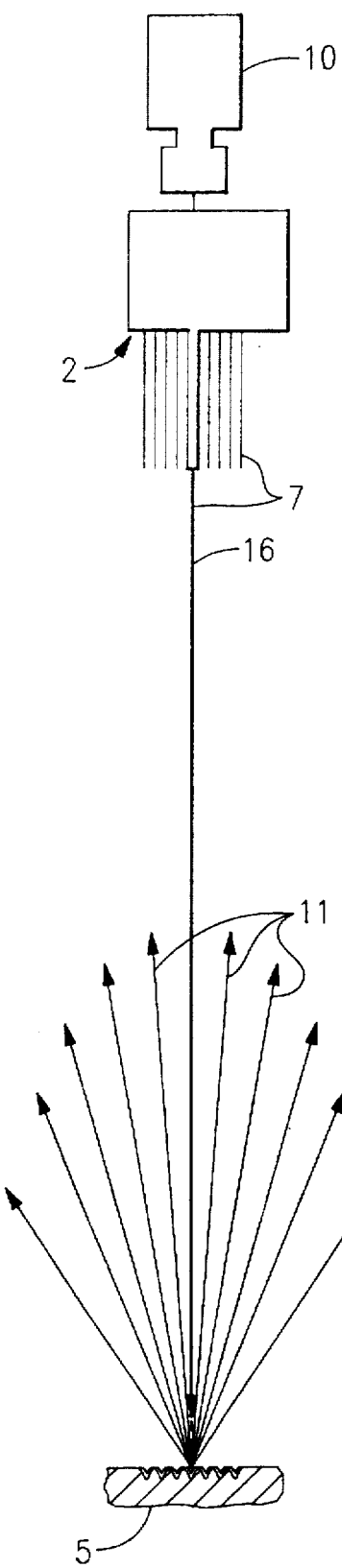
FIG. 4B diagrammatically shows the reflection by an object of the collimated light supplied to a diffuse area.

With reference now to FIGS. 3 and 4A and 4B, a brief discussion concerning the specular and the diffuse reflection characteristics will now be provided. As can be seen in FIG. 3, the object to be observed 12 has both specular areas 3 and diffuse areas 5. The supplied light rays 7 (FIG. 3, 4A and 4B) from a continuous diffuse light source 2 are reflected quite differently depending on which area the light rays 7 contact on the object to be observed 12. In the case of the supplied light rays 7 contacting specular area 3, the reflected light rays 9 are reflected back toward the light source along the observation axis 16 essentially parallel to and at a substantially equal intensity as the supplied light rays 7. Thus, the reflected light rays 9 are easily and accurately sensed by a video camera or some other observation or imaging device 10.

When the supplied light rays 7 contact a diffuse area 5, the supplied light rays 7 are reflected by the diffuse area 5, due to its surface geometry and composition, at a plurality of different angles and in a plurality of different directions as reflected light rays 11, e.g. the reflected light is scattered or dispersed in a variety of different directions. Accordingly, only a minor or relatively smaller portion or amount of the supplied light rays 7 is reflected back along the observation axis 16 parallel to the supplied light rays 7. The reflected light rays 11, returned along the observation axis, are also sensed by the observation device but are sensed as being at a significant lesser intensity than the intensity of the supplied light rays 7 or the intensity of the light rays 9 reflected by specular areas 3.

Stated simply, the light rays 9 reflected by specular areas 3 are essentially at the same intensity as the supplied light rays 7 and thus only diminishes minimally the further the imaging device 10 is located along the observation axis 16 from the object to be observed 12. This light rays 11 reflected by the diffuse areas 5, on the other hand, diminish substantially with distance the further the imaging device 10 is located along the observation axis 16 from the object to be observed 12. This reflection principle of the diffuse areas is commonly referred to as the "Inverse Square Law" any diverging field, including light, decreases as the inverse square of the distance from the source—in this instance the diffuse area.

The above generalizations are true except for optical effects in the local surface geometry at the point of reflection. For example, the specular reflection of a flat area, e.g. a heat seal, retains its intensity with distance while the reflection from a concave specular surface concentrates and increases in intensity until the reflection reaches a focus after which the reflection diverges and decreases in intensity. A reflection from a convex specular surface simple diverges and decreases in intensity with distance.

An important feature of the present invention is that at least some light from 100 percent of the desired surface area to be imaged and which is located within the region of interest ROI is reflected back along the observation axis 16 so that the imaging device 10 is able to image 100 percent of that surface area. This facilitates computer processing of the sensed optical image into usable information concerning 100 percent of the desired surface being observed and located within region of interest ROI. If a portion of the surface area being observed does not reflect any light back to the imaging device 10, the imaging device is not able to determine whether all of the reflected light is being reflected away from the observation axis, due to a geometric aberration in the reflective surface geometry of that area, or whether the light is passing through a defect in the surface of the object, e.g. a hole. When reflected light is not received from the entire region of interest ROI, the imaging device is only able to determine either the presence or absence of a particular area being imaged, i.e. reflected light is received or reflected light not is received. If light is reflected from 100 percent of the desired surface being observed, then the imaging system can discern not only the presence or absence of each area of interest of the object being observed, but can also discern a particular surface characteristic about each area of interest.

The present inventor has appreciated that by controlling a variety of operational parameters of an imaging system, the variation in intensity of the light reflected by the surface of the object to be observed 12 and sensed or imaged by the observation device can be utilized to determine location, shape, arrangement, boundaries, boarders, etc. between specular areas and diffuse areas, e.g. the boundary between a glued area and an unglued area of a piece of cigarette paper. This information can be very useful in controlling production or manufacturing equipment.

An important aspect of the present invention is that the co-axially illumination source must be wide enough to reflect specularly from all points of the region of interest ROI of the object to be observed 12, but positioned far enough away from a top surface of the object to be observed 12 so that the specularly reflected light 9, from the object 12, overwhelms the diffusely reflected light 11 to such a magnitude that sensing device 10 is readily able to distinguish the specular areas from the diffuse areas or the boarders or boundaries between such areas. In particular, it is desirable to have the intensity of the specularly reflected light be at least 10 percent greater than the intensity of the diffusely reflected light, more preferably at least 30 percent greater, and most preferably at least 50 percent greater.

Turning now to FIG. 5, a continuous diffuse illumination device 2, according to the present invention, is particularly suitable for use with a computer controlled robotics assembly or other manufacturing apparatus 6 that utilizes a video camera 10, equipped with a lens, to image an object 12 on a support table, conveyor or other support surface 14 by viewing the object along an observation axis 16. With such a robotics apparatus, electronic signals from the camera 10, resulting from the image of the object 12, are used to control a computer 4 which, in turn, controls the operation of a robotics assembly or other manufacturing or inspection apparatus 6. The object 12 may be a continuous length of a product or may be a plurality of individual components supported on the movable table, conveyor or moveable jig 14 constituting a part of the robotics or manufacturing apparatus permitting the object to be very accurately viewed along the observation axis 16.

As shown in FIGS. 5, 6, 10 and 11, a metal or plastic housing 18 encases the various components of the continuous diffuse illumination device 2. The housing 18 comprises a first pair of spaced apart parallel side walls 19, a second pair of spaced apart parallel side walls 20 and a roof wall 21 and a base wall 21'. An aperture 22 is formed in both the roof wall 21 and the base wall 21' (except for FIG. 6) and the two apertures 22 are concentric with one another and spaced apart from one another along the observation axis 16. The housing accommodates therein at least one light source 28 adjacent one of the side walls 19, a beam splitter 23 is located remote from the light source 28 and positioned, at an inclined orientation, along the observation axis 16, a light diffuser, shown generally as 24, is located between the light source 28 and the beam splitter 23, and a light trap 26 is carried by the side wall 19 opposite the side wall 19 adjacent the light source 28 (except for FIG. 6). The arrangement of these components is such that the light source 28 casts light upon the diffuser 24 which, in turns, diffuses the light from the light source 28 and casts the diffused light upon the beam splitter 23 which reflects a desired portion of the diffused light toward the object 12. Any unreflected light which passes through the beam splitter 23 is absorbed by the light trap 26 located adjacent the beam splitter 23.

The beam splitter 23 has a partially reflective first surface 27. A desired portion of the light e.g. approximately half of the light from the diffuser 24 impacting upon the reflective first surface 27 of the beam splitter 23, is reflected toward the object 12, while the remainder of the light passes through the beam splitter 23 and is absorbed by the light trap 26. Likewise, a portion of the light reflected back by the object 12 is transmitted toward and through the beam splitter 23 along the observation axis 16 for viewing by the observation device or camera 10 while a portion of the light is reflected by the beam splitter 23 back toward the diffuser 24. The light supplied to the camera 10 is used to determine the precise shape, orientation, intensity, boundary, border and/or any other optical characteristic of the object 12. It is well known in this art how to utilize the light supplied to the camera 10 to sense, image, and/or otherwise determine the precise shape, orientation, intensity, boundary, borders and/or other optical characteristic of the object 12, e.g. via associated hardware and software, and thus a further detail description concerning the same is not provided herein.

If desired, the diffuser 24, of the embodiments of FIGS. 5 and 10, can be angled back away from the observation axis 16 to facilitate shielding of the diffuser 24 from the object 12 to be observed. Such angling of the diffuser 24 prevents the diffuser 24 from directly illuminating the object to be observed.

Figure 6:
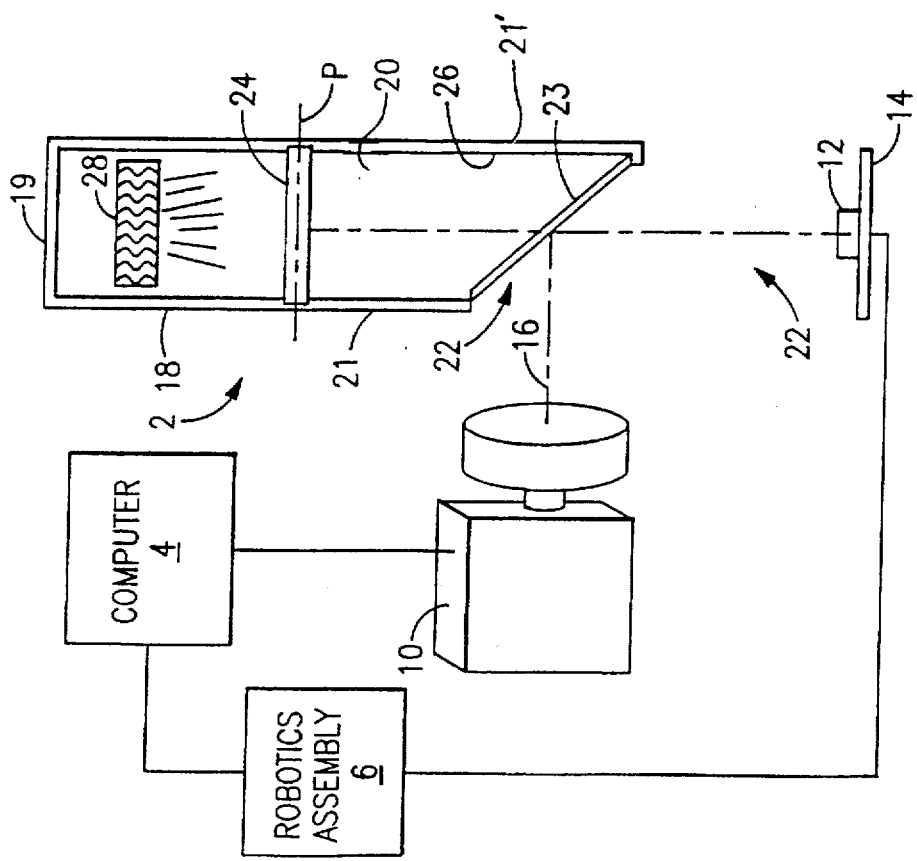
FIG. 6 is a diagrammatic illustration of a further embodiment of the improved continuous diffuse illumination device, equipped with an inspection camera, in which the diffuser is "concealed" from the object being observed.

The embodiment of FIG. 6 is slightly different from the embodiment shown in FIG. 5. In this embodiment, the position of the observation device 10 and the diffuser 24 and light source 28 are switch. That is, a portion of the supplied diffuse light will passes directly through the beam splitter 23 toward the object 12 and a portion of the light reflected by the object 12 is reflected by the beam splitter 23 toward a lens of the observation device 10 for imaging. According to this embodiment, the location of the light trap 26 is modified and absorbs the supplied light which is initially reflected by the beam splitter 23. The two aperture 22 are located adjacent one another and lie in planes that extend normal to one another. By this arrangement, the beam splitter 23 completely shields the diffuser 24 from the object to be observed 12.

The diffuser 24 may be formed of treated glass, plastic, or some other light translucent material capable of evenly diffusing light cast upon the diffuser by the light source. The diffuser 24 may alternatively be formed of an etched or ground glass, or may be formed of opal glass having light scattering centers of colloidal particles. Frosted glass, milky plastic or a Murata screen may also be used. Murata screen is formed of a diffusing synthetic plastic material.

The diffuser 24 can be either a single diffuser member or a plurality of members. The interior surface of the housing 18 may be painted or coated with a reflective substance which is selected to reflect light which is substantially equal in intensity and character to the light reflected by the beam splitter 23 so as to facilitate uniform illumination of the object to be observed.

It is important that the diffuser 24 have wide-angle diffuser characteristics so that light cast thereon is evenly diffused by the diffuser. This ensures that a substantially uniform intensity of light passes through the diffuser for reflection toward the object 12 by the beam splitter 23.

The light source 28 is either a single source of light or comprises a plurality of light members. A variety of different light sources may be used as the light source 28. For example, the light source may be a rectangular configuration having a plurality of bulbs evenly spaced thereon. Alternatively, the light may be incandescent, fiber optics, LEDs or fluorescent. An important requirement of the light source 28 is that it is capable of supplying a substantially uniform intensity of light to the diffuser 24 so that the diffuser 24 may evenly diffuse the light received from the light source 28 and uniformly illuminate the object 12 both along the observation axis and at an angle to the observation axis. The entire inner surface of the housing 18, including the inner surface to the right of the diffuser 24 in FIGS. 5 and 10 and above the diffuser 24 in FIG. 6, is preferably coated with a substance, e.g. paint, which promotes reflection of the light generated by the light source.

The beam splitter 23 is preferably in the form of a mirror beam splitter that is well known in the art, but it also could comprise a cube or a membrane. The second surface 34 of the beam splitter 23, e.g. the surface facing the camera 10, has an anti-reflection coating disposed thereon to prevent stray light from being reflected toward the camera 10 and thereby create a false image. Preferably, magnesium chloride (MgCl) is used as the anti-reflection coating on the beam splitter 23. It is to be appreciated that any other suitable anti-reflection coating, that permits the camera 10 to observe the object 12 through the beam splitter 23 free of a double image or a ghost image, may be utilized on the second surface 34 of the beam splitter 23.

Preferably, the beam splitter 23 is disposed at an angle of 45° with respect to the observation axis 16, however, it will be appreciated that the angle of the beam splitter may be varied, as desired, from a 45° orientation and still function in the desired manner. If the beam splitter 23 is located at a 45° orientation with respect to the observation axis 16, it is necessary to approximately double the length of the side walls 19 and 20 to achieve substantially uniform illumination of the object 12. If the orientation is varied from the 45° orientation, the length of the side walls 19 and 20 would be accordingly varied in order to provide uniform lighting of the desired area of the object 12. The length of the side walls is determined such that the continuity of incident light, which falls on the object, is substantially uniform. In addition, the size, shape and orientation of the object 12 to be observed must be taken into account, along with any tilt angle of the diffuser with respect to the observation axis, when determining the length to the side walls.

Figure 7:
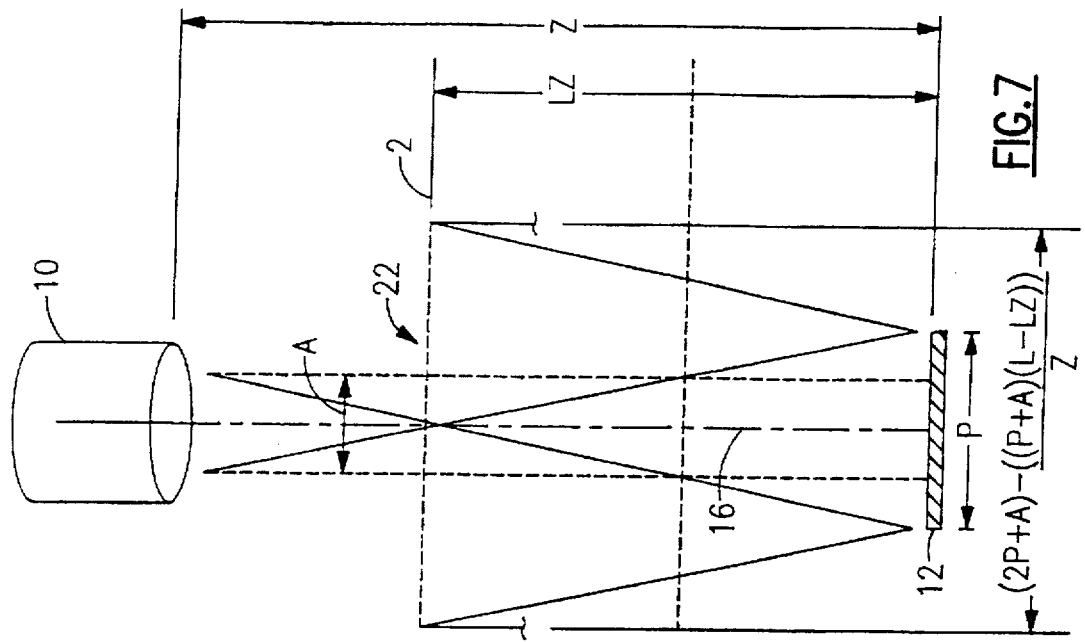
FIG. 7 is a diagrammatic view showing the parameters used to calculate the aperture size of an appropriate illumination device.

For flat planar surfaces (see FIG. 7), the following formula can be used to calculate the proper minimum size of the illumination device.

Minimum Illumination $$\text{Device Aperture Size} = (2P+A) - ((P+A)(Z-LZ)/Z)$$

Where:

A = the entrance pupil diameter of the lens;

P = the object (field-of-view) width;

Z = the distance between the lens and a top surface of the object measured along the observation axis; and LZ = distance from the top of illumination device to the top of object measured along the observation axis.

It is to be noted that the first portion of the formula, namely (2P+A), alone describes the proper size of the aperture of the illumination device when the top of the illumination device is located at substantially the same distance from the object 12 to be observed as the camera lens. The second term, namely ((P+A)(Z−LZ)/Z), specifies that the illumination device becomes smaller in size as the top portion of the illumination device 2 approaches the object 12 to be observed, i.e. the illumination device 2 is located adjacent the object 12 to be observed and remote from the camera lens.

The above formula is very useful for determining an illumination device aperture size for viewing flat reflective planar surfaces. For uneven surfaces, the inventor has not yet derived any precise formula for calculating an optimum illumination geometry. Therefore, a bit of trial and error may be required to find the best solution to achieve uniform illumination of the object. It should also be borne in mind that the further the illumination device is from the object 12 to be observed, the more the illumination device functions like a point light source.

Figure 9:
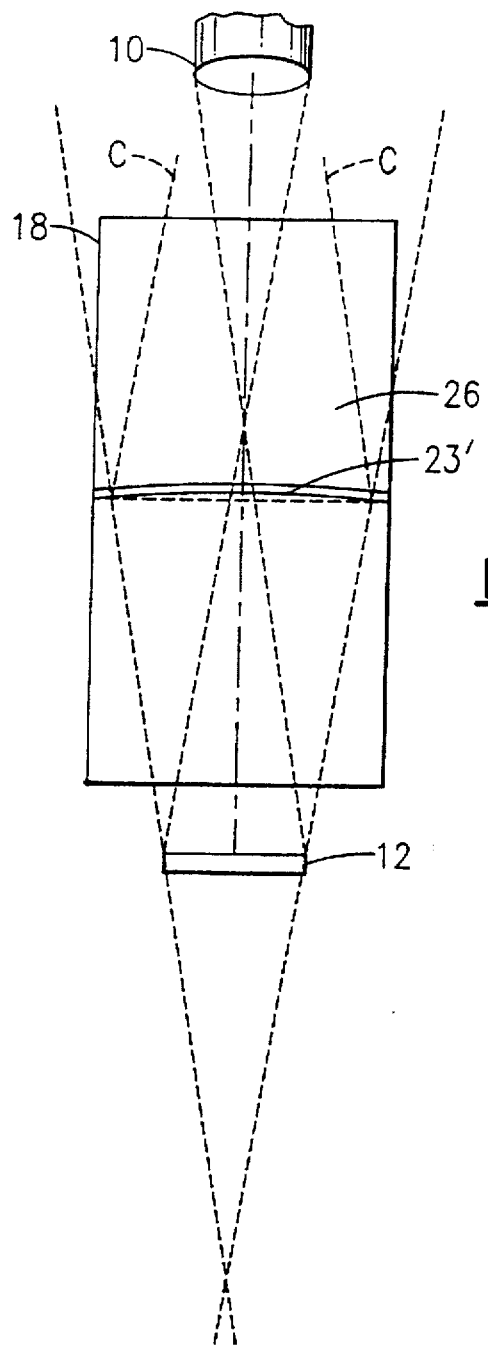
FIG. 9 is a diagrammatic cross-sectional illustration of an object and camera employing the curved beam splitter of FIG. 8 and showing its optical effect.
Figure 8:
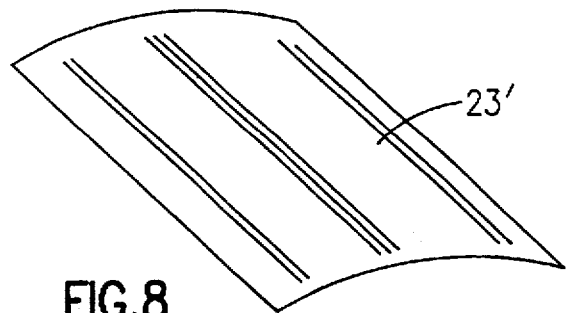
FIG. 8 is a diagrammatic perspective illustration of a curved beam splitter according to the present invention.

For maximum uniformity of illumination, the beam splitter 23' should be curved sufficiently (FIGS. 8 and 9) to eliminate the beam splitter 23' from reflecting undesired light, i.e. the beam splitter 23 ' only reflects light directed toward the beam splitter and does not reflect any light reflecting off the adjacent side walls 20, 21, 21'. In the case of an illumination device 2 having two-inch square apertures and a beam splitter inclined at an angle of 45° with respect to the object, the calculated radius of curvature required is 11.482 inches, which is just sufficient to cause diverging rays to be collimated from the beam splitter 23' back to the diffuser for a 2 inch square aperture. The required curvature is a function of the camera 10 and the part 12 distance, however, the dimensions shown in FIG. 9 represent a good approximation of a typical case. As a rule of thumb, then, the radius of curvature of the beam splitter 23 should be slightly less than 11.242/2=5.621 or, to be safe, a radius of about 5.5 times the aperture dimension. This can be achieved with a flexible beam splitter by making the width of the beam splitter be between 101% and 102% of its nominal flat width, and then fitting the oversize beam splitter within its original nominal width holding fixture, thereby flexing the beam splitter to the desired partially cylindrical curvature.

The light trap 26 may consist of a planar panel defining a straight wall parallel to the observation axis 16. The light trap 26 is preferably of a flat black color so as to be capable of maximum light absorption. Alternative, a portion of the inner surface of the side wall 19 may be painted black, for example, to function as the light trap. By locating the light trap in optical alignment with the diffuser 24 and the beam splitter 23, supplied light from the diffuser 24 passing through the beam splitter 23 will be absorbed by the light trap 26 and will not be reflected or supplied to the camera 10 where it could produce an erroneous signal.

A portion of the light diffused by the diffuser 24, e.g. 50%, will be reflected by the beam splitter surface 27 in a uniform manner upon the object 12. This uniform illumination of the object 12, in a symmetrical relationship of light supplied along the observation axis 16, permits the camera 10 to produce a highly accurate and unambiguous image of the object 12 free of spurious glints and shadows thereby to precisely view and determine the exact location, orientation and other visual qualities of the object being observed, particularly for shiny and uneven surfaces. This facilitates accurate robotics positioning control and manipulation of the object 12.

With reference now to FIG. 10, a modification of the present invention will now be described. This embodiment is essentially identical to the embodiment disclosed in FIG. 5 and thus identical components are given identical reference numbers. The only difference between this embodiment and the embodiment of FIG. 5 is that the continuous diffuse illumination device 2 of FIG. 10 is provided with a light barrier 40. The light barrier 40 is connected or otherwise secured or fastened, at 46, to a lower surface of the continuous diffuse illumination device 2, i.e. base wall 21'. An opposite end of light barrier 40 is provided with an aperture 48 which is at least the same size and preferably larger than apertures 22 and is optically aligned with the apertures 22 of the illumination device 2. The light barrier 40 has an exterior surface 44 and an interior surface 42 which are both continuous and generally opaque. At least the interior surface 42 is painted or otherwise constructed so as to absorb any light contacting the interior surface, i.e. this surface functions as a light trap and absorbs light.

The light barrier 40 can be constructed from a variety of different materials and can be made into a variety of different shapes as long as the barrier is constructed to prevent any light from the surrounding environment directly illuminating the object 12 to be observed. The light barrier 40 is designed so that essentially only light supplied by the illumination device, along the observation axis 16, illuminates the object 12 to be observed. It is to be noted that a small amount of surrounding environment light, illuminating the side surfaces 51 of the object 12 to be observed (FIG. 10) can be tolerated as long as surrounding light does not significantly interfere with the continuous diffuse illumination of the top surface area of the object 12 to be observed and located within the region of interest. Accordingly, the base 50 of the light barrier 40 must be placed as close as possible to a top surface of the object 12 to be observed, e.g. a fraction of an inch or so, to minimize any illumination interference from the surrounding light.

Figure 12:
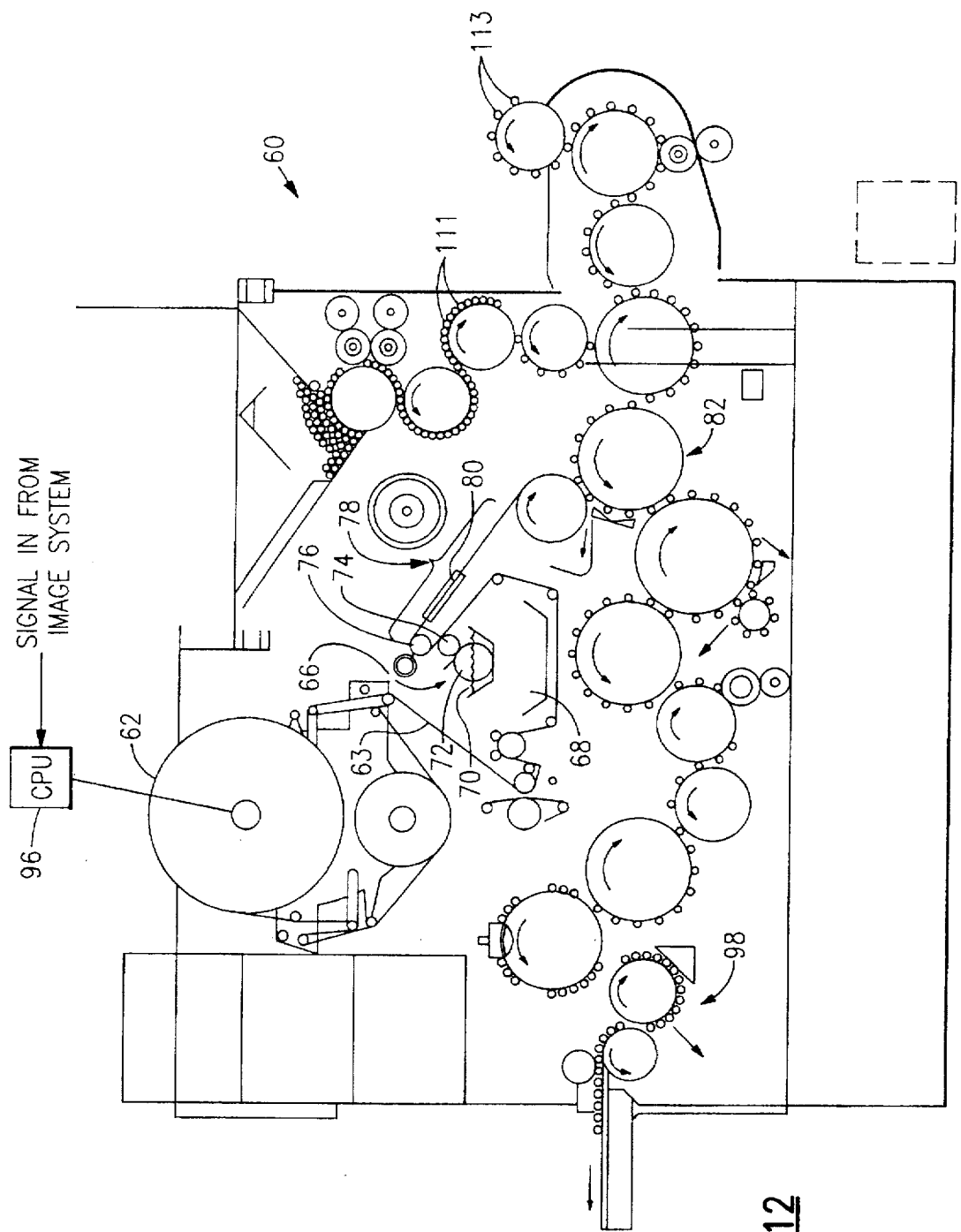
FIG. 12 is a diagrammatic side elevational view of a conventional cigarette rolling device.

With reference now to FIG. 12, a brief description concerning a prior art cigarette manufacturing device will now be provided. As can be seen in this figure, the cigarette manufacturing device is generally designated as 60. As the present invention is only relevant to the inspection of the cigarette paper following the application of glue to one surface thereof, a brief description concerning the overall cigarette manufacturing process will be provided and this will be followed by a detailed description of the system for inspecting of the glued applied to the cigarette paper.

An elongate continuous roll of cigarette paper 62 is supported on a rotatable axle of the device 60 and a leading end of the continuous roll of cigarette paper is conveyed along the device, via numerous cylindrical transfer rollers (not separately numbered), to a glue application station 66. The glue application station 66 comprises a tank 68 which holds a supply of suitable glue 70. The glue is maintained at a constant level in the tank by pumping additional glue from a supply area, not shown in detail. As such continuous supply of glue is well known in the art, a further detailed description concerning the same is not provided herein.

A first roller 72 is partially immersed within the tank 60 so that as the roller 72 rolls within the tank 68, it picks up a desired quantity of the glue 70 on the exterior surface thereof. The glue 70 is then transferred from the first roller 72, via a contact transfer, to an exterior surface of a smaller glue applicator roller 74. As the glue applicator roller 74 rotates, its exterior surface comes into contact with a top surface of the sheet of cigarette paper 63 and transfers the glue 70 thereto. The exterior surface of the applicator roller 74 is contoured or configured such that the roller only contacts the desired areas where glue is to be applied, while the exterior surface of the applicator roller 74, where no glue is to be applied, is spaced from the surface of the cigarette paper 63 so that no glue is transferred to those areas of the cigarette paper. After the glue is transferred from the glue applicator roller 74 to the continuous cigarette paper 63, the web of cigarette paper 63 is conveyed around a return roller 76 and to an area 78 where it is possible to inspect the sufficiency of the glue 70 applied to the cigarette paper 63, prior to the cigarette paper being rolled with two pre-rolled tobacco components 113 and a filter 111 into a finished cigarette product at a rolling station 82.

Located between the rolling station 82 and the return roller 76 is a heater section 80 which applies a desired amount of heat to at least one surface of the continuous web of cigarette paper 63, e.g. a bottom surface, to partially activate the glue to facilitate bonding thereof once the cigarette paper 63 is formed into a finished cigarette product at the rolling station 82. Assuming that the glue 70 is sufficiently applied to a segment S of cigarette paper 63 (see FIG. 13A), the glued cigarette paper is thereafter rolled with two pre-rolled tobacco components 113 and a filter 111 into a finished cigarette product. Thereafter, the product is cut at its center to form two final cigarette products. As the remaining features and process of the cigarette manufacturing device are conventional and not relevant to the present invention, a further detailed description concerning the same will not be provided.

It is to be noted that due to the basic construction of the cigarette rolling device 60, only a small inspection area 78, following application of the glue but prior to the glued cigarette paper entering the rolling station 82, is provided for inspecting the location and adequacy of the glue applied to the cigarette paper 63. This confined area minimizes the possible amount of suitable lighting and inspection devices which could be utilized to illuminate the cigarette paper 63 to evaluate the glue application.

Figure 13A:
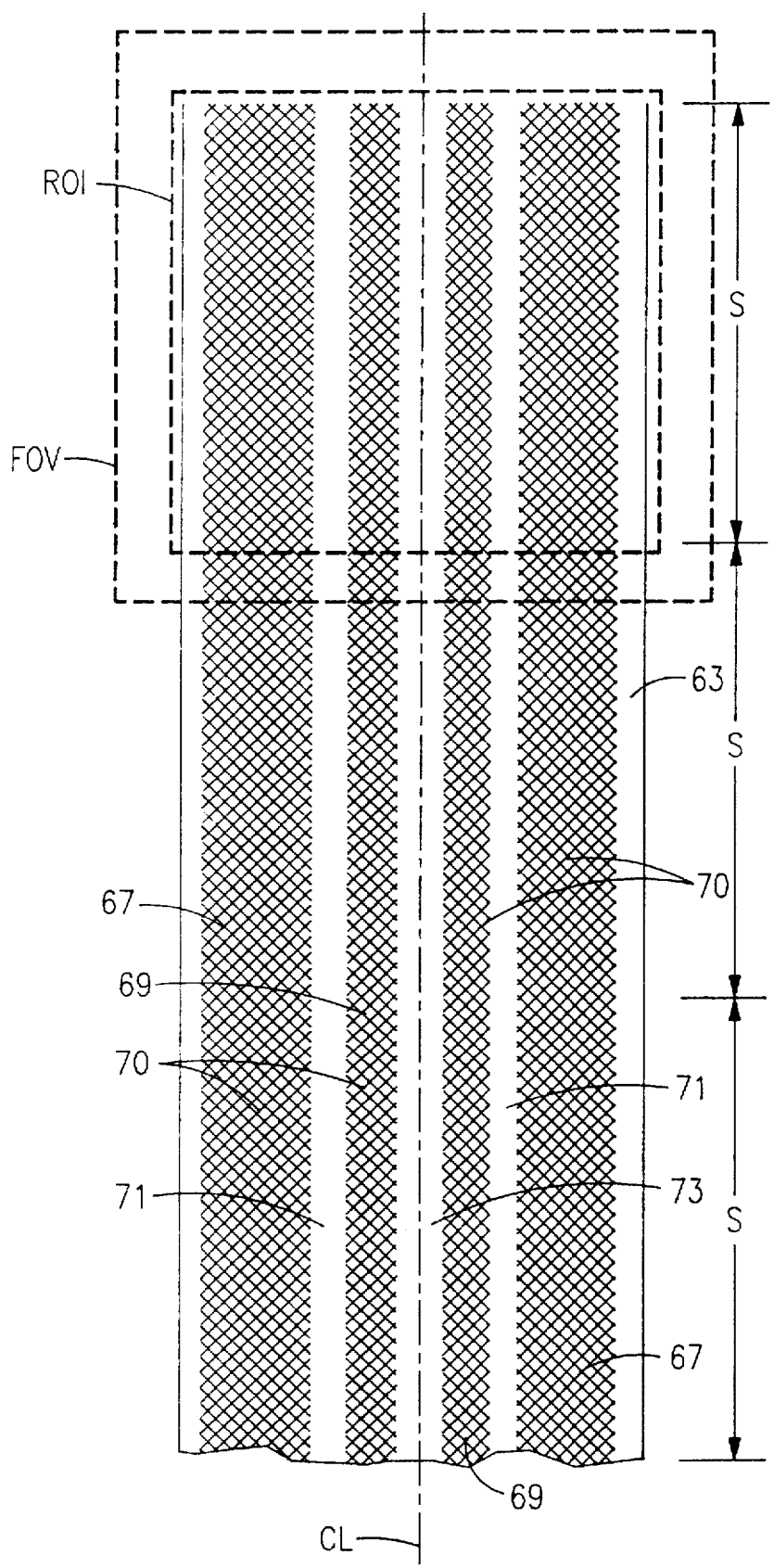
FIG. 13A is a diagrammatic top plan view of the cigarette paper, following the proper application of glue but prior to rolling the cigarette paper into a finished cigarette product.

FIG. 13A shows a top plan view of a cigarette paper which has the glue 70 applied thereto in a desired quantity and at the desired locations. As can be seen this figure, the glue is applied along a pair of wider lateral longitudinal strips 67 which are each spaced from, but adjacent one longitudinal edge of the cigarette paper, e.g. each strip has a width approximately one-half of an inch or so. The glue 70 is also applied along two narrower central strips 69 running longitudinally along but spaced a small distance on either side of a center line CL of the cigarette paper, e.g. each central strip has a width of approximately one-quarter inch or so. Finally, there is also one central unglued region 73 and two unglued lateral regions 71, one located between the wider lateral longitudinal strip of glue and the narrower central strip 69 of glue and the other located between the second wider lateral longitudinal strip 67 of glue and the second narrower central strip of glue.

Figure 13B:
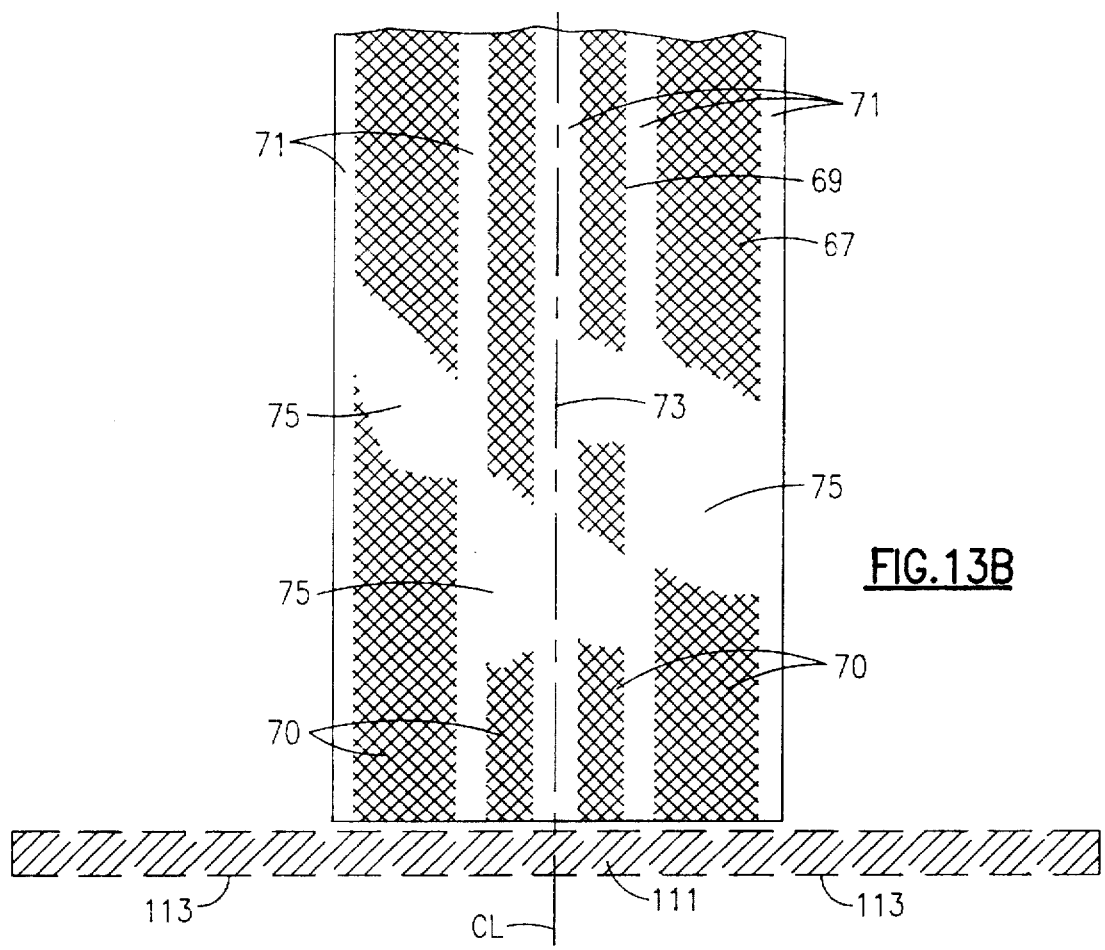
FIG. 13B is a diagrammatic top plan view of a portion of the cigarette rolling paper, following application of the glue, showing a defective glue application with a double-wide filter and two pre-rolled tobacco components shown in dashed lines.

A plurality of laser holes (not visible) may be formed in the unglued lateral regions 71 of the cigarette paper 63 to the facilitate the passage of air into the filter when a consumer is smoking the finished cigarette product. Such laser holes facilitate the appropriate blend of fresh air and tobacco smoke which is desired by consumers. The unglued central region 73 facilitates cutting of the cigarette paper 63, along center line CL, into two separate pieces, e.g. prevents the cutting knife from being gummed up. It is to be appreciated that the cigarette paper shown in FIGS. 13A and 13B are sized to form two separate cigarettes, e.g. a double wide filter 111 is arranged in a central region of the cigarette paper and a pre-rolled tobacco component 113 extends perpendicularly from each longitudinal edge of the cigarette paper 63 with an end of the pre-rolled tobacco component 13 abutting each opposed end of the double wide filter 111 (FIG. 13B). Once the cigarette paper 63 is rolled with the filter 111 and tobacco components 113 into an elongate cylindrical member, at rolling station 82, the elongate cigarette product is cut in half to form two cigarettes. A supply of pre-rolled tobacco components 113 and filters 111 are continuously conveyed to the rolling station 82 by a plurality of unnumbered transfer rollers. The rolling station 82 rolls the cigarette paper 63 around one filter 111 and two pre-rolled tobacco components 113, once arranged as shown in FIG. 13B, into a final cigarette product.

Figure 14:
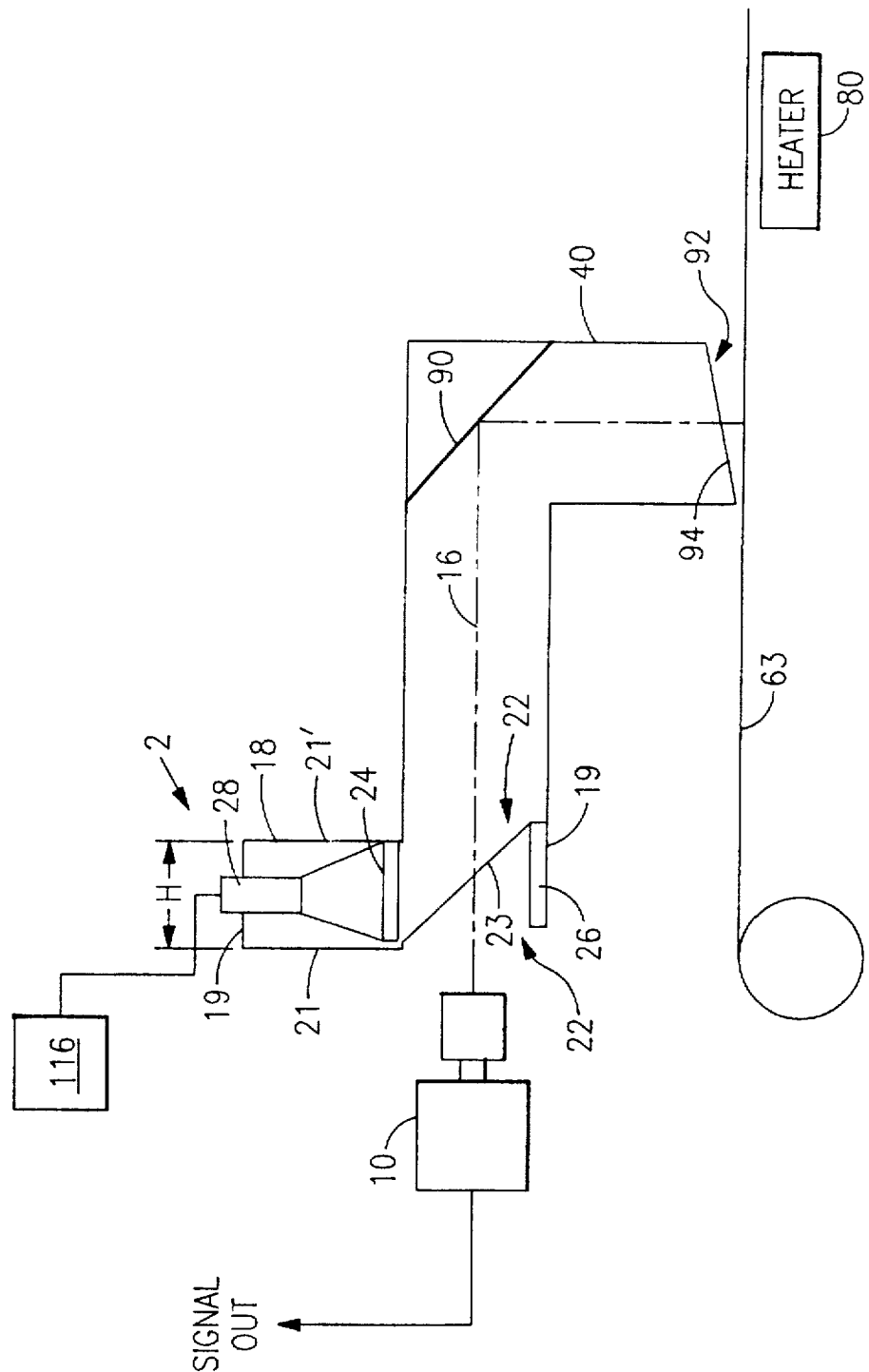
FIG. 14 shows an application of the present invention for inspecting a continuous web of cigarette paper following application of the glue but prior to rolling.

Turning now to FIG. 14, the device for inspecting the applied glue will now be discussed. The device comprises a housing 18 which encases the various components of the continuous diffuse illumination device 2. The housing 18 comprises a first pair of spaced apart parallel side walls 19, a second pair of spaced apart parallel side walls 20 (only one of which is shown in this figure) and a roof wall 21 and a base wall 21' are separated by a distance, i.e. height H. An aperture 22 is formed in both the roof wall 21 and the base wall 21' and the apertures 22 are concentric with one another and located along the observation axis 16. The housing accommodates therein at least one light source 28 adjacent one of the side walls 19, a beam splitter 23 located remote from the light source 28 and positioned along the observation axis, a light diffuser, shown generally as 24, is located between the light source 28 and the beam splitter 23, and a light trap 26 is supported by the side wall 19 opposite the side wall 19 adjacent the light source 28. The arrangement of these components is such that the light source 28 casts light upon the diffuser 24 which, in turn, diffuses the light from the light source 28 and casts the diffuse light upon the beam splitter 23 which reflects a desired portion of the diffuse light toward the object 12. Any unreflected light, which passes through the beam splitter 23, is absorbed by the light trap 26 located adjacent the beam splitter 23.

A light barrier 40 surrounds or encases the observation axis 16 to ensure that substantially only the light supplied by the light source 28 illuminates the top surface of the cigarette paper 63, having the glued and the unglued areas, and thereby prevents any optical interference by light from the surrounding environment.

It is to be noted that a mirror 90 is provided along the observation axis 16, in this embodiment, to reflect the light supplied by light source 28 at a 90° angle toward the top surface of the cigarette paper 63, i.e. a first portion of the observation axis 16 extends parallel to the cigarette paper 63 while the second portion of the observation axis 16 extends perpendicular to the cigarette paper 63. This mirror 90 is arranged at an angle of 4520 with respect to the observation axis 16 and facilitates location of the imaging device in limited or confined areas, such as that of the cigarette manufacturing device 60 discussed previously. It is to be appreciated that additional mirrors may be employed to facilitate altering of the observation axis so that a desired inspection can be achieved in virtually any application.

The light barrier 40 defines an aperture 92 in a base portion thereof which is positioned immediately adjacent the top surface of the cigarette paper 63 to which the glue was just applied. In order to prevent the substantial amount of dust created within the cigarette manufacturing device 60 from hindering inspection of the cigarette paper 63, a piece of glass 94 seals, e.g. hermetically, the aperture 92 formed in the base of the light barrier 40. This glass 94 prevents or minimizes the possibility of any dust migrating into the light barrier 40 or along the observation axis 16 to affect the sensing or viewing of the imaging system. It is to be noted that the glass should be oriented at an angle of approximately 80°, with respect to the observation axis, to prevent the glass from reflecting the supplied light back to the observation device and generating a false reading.

Figure 13C:
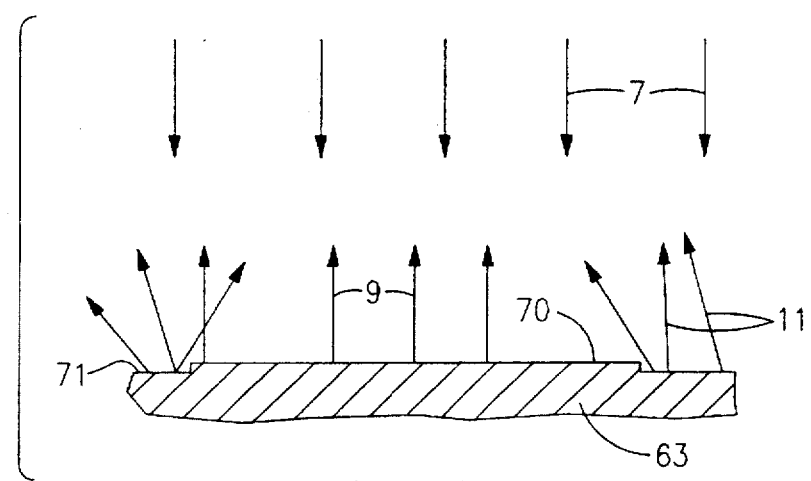
FIG. 13C is a diagrammatic partial cross-sectional view of FIG. 13A showing the reflection of the supplied light by both the glued specular areas and the unglued diffuse areas.

If the continuous diffuse light contacts a strip of glue 70 (FIG. 13C), i.e. a specular region, the light is reflected back along the observation axis 16 toward the observation device 10 at an intensity such that the reflected light rays 9 are sensed as being at substantially the same intensity as the supplied light 7. The light supplied to the untreated or unglued areas of the cigarette paper 71, 73, i.e. a diffuse region, is diffused by the unglued cigarette paper regions so that only a minor portion of the supplied light is reflected back along the observation axis 16 toward the observation device 10 and the intensity of the reflected light rays 11 is sensed as being of a substantially less intensity than the intensity of the supplied light 7 and the reflected light rays 9 of the glue area. The diffuse areas disperse or scatter the supplied light in a plurality of different directions and at a variety of different angles and thus only a substantially smaller amount of light is reflected back along the observation axis 16.

To assist with observing and maintaining control of the production of the cigarettes, the light source 28 is provided with a strobing device 116 so that the supplied light is strobed, e.g. at 60 hertz/60 frames per second. During each strobe cycle, the imaging system is viewing a segment S of cigarette paper (FIG. 13A) approximately two and one-half inches long and three inches wide, i.e. the region of interest ROI. For such application, the field of view FOV should be roughly about 10% larger or about two and three-quarter inches long and three and one-quarter inches wide. The strobing of the light is adjusted so that the imaging system will sequentially view the entire length of the continuous web of cigarette paper 63 approximately two and one-half inches at a time.

When the imaging system determines that there is a defect in the location and/or amount of glue applied, or a lack of glue at a desire location 75 (FIG. 13B), a signal is generated by the device and sent to a central processor 96 controlling operation of the entire cigarette manufacturing device 60. This signal indicates that an inspected section S of cigarette paper 63 is to be rejected and the central processor 96, accordingly, will monitor the progress of that reject section of cigarette paper as it progresses through the cigarette manufacturing device 60 and will appropriately reject the cigarette(s) formed from that section of improperly or insufficiently glued cigarette paper at an appropriate time, i.e. at the reject station 98. The signal is typically placed in a shift register and monitored by the central processor 96 until it is determined that the defective cigarette(s) is located at the reject station 98. Once the defective cigarette(s) is at such location, it is automatically rejected. As such teaching is well known in the cigarette manufacturing art, a further detailed discussion concerning the same is not provided.

Figure 15A:
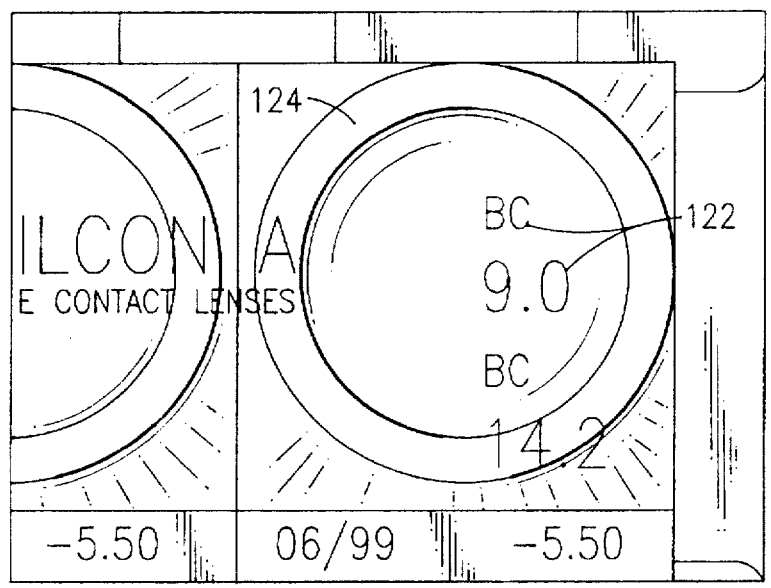
FIG. 15A shows an image of a seal, from a foil side of a packaging material, with the imaging system being position too close to the seal so that the art work is still visible.
Figure 11:
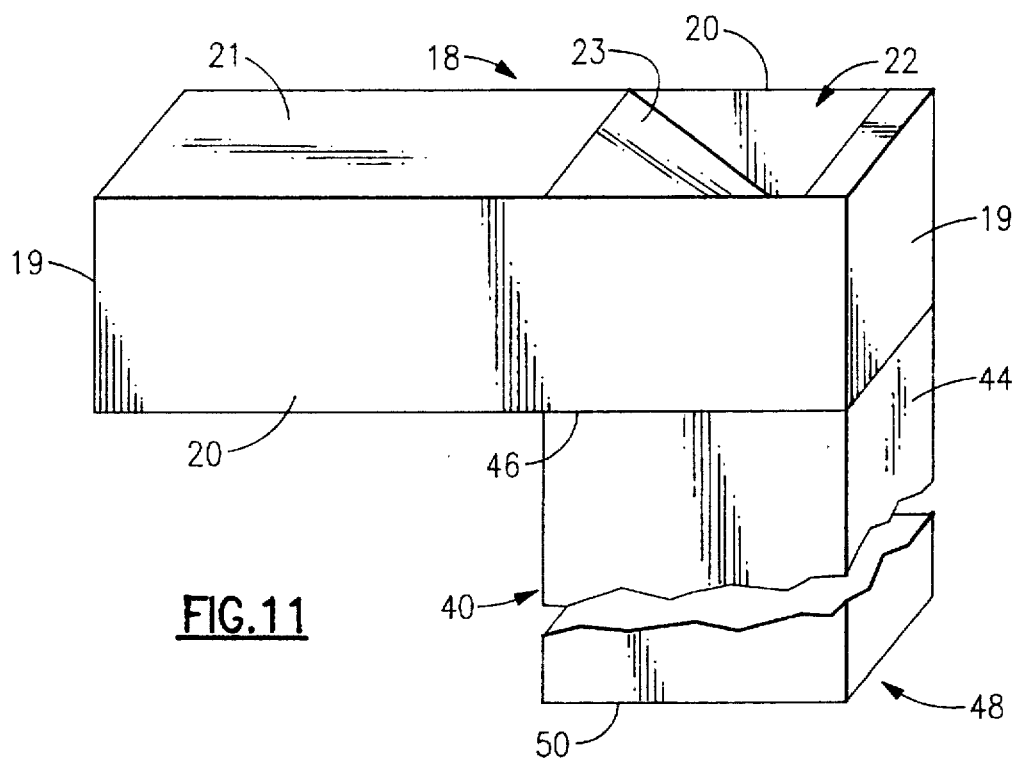
FIG. 11 is a diagrammatic perspective view of the continuous diffuse illumination device of FIG. 10 with the light barrier.

With reference now to FIGS. 15A and 15B, two images of a seal, from a laminated printed side of the packaging, are shown which were generated in by illumination in accordance with the prior art (FIG. 15A) and illumination in accordance with the imaging techniques of the present invention (FIG. 15B). The laminated printed surface has black and white art work 122 (FIG. 15A) thereon which is randomly positioned on the packaging material. The diffusely reflecting black and white art work 122 underlies a clear high-gloss finish which readily reflects ambient light. The laminated printed surface is relatively flat within and adjacent seal area 124 and randomly wrinkled outside the seal area.

Due to the high contrast of the black and white art work 122 appearing randomly on the packaging material surface, the only physical attribute of the seal surface which distinguishes the heat seal area 124 from the remaining surrounding area is the difference in surface geometry of the two areas. The heat seal is relatively consistent in form—being flat or slightly concaved upward. The surrounding area is randomly fluctuating with the only consistent feature being the relatively short, steep slope appearing intermittently at the heat seal boundary. These two features of the heat seal process, (1) the intermittent steep slop at the seal boundary and (2) the consistent near-flatness of the heat seal area, are the key geometric attributes by which one is able to distinguish the two areas from one another.

According to this application, the laminated printed art work 122 can be illuminated such that the art work can be made to essentially "disappear" (see FIG. 15B) so that the only visual features apparent to the observation device are the features indicative of the difference in surface geometry which can be readily perceived by the camera 10. As the art work pigments beneath the foil surface either absorb or diffusely reflect the light, their intensity decreases inversely with the square of the distance of the light source and the camera from the surface. The gloss surface 124 overlying the diffusely reflecting art work, however, reflects light specularly such that the apparent intensity of such gloss surface remains essentially constant with distance provided that the local surface geometry allows directs specular reflection of light from the light source to the observation device. By providing a co-axial illumination source which is wide enough to reflect light specularly from the entire central region of the heat seal area and by positioning the light source far enough away from the seal area so that the specular reflected light overwhelms the diffusely reflected light, the underlying art work 122 can be rendered essentially "invisible".

Depending upon the material being handled and the seal process tolerances, a circular area of a desired width can be defined which can be presumed to always appear illuminated within the seal area of the field of view FOV. A radial caliper array can be programmed, with the origin 126 of each caliper lying within a "guaranteed flat" zone of the seal area. A first light-to-dark edged detected by moving radially inward (FIG. 16A) from the origin of each caliper can be assumed to be a measurement of the inner seal edge. A first light-to-dark edge detecting by moving radially outward from the origin of each caliper can be assumed to be a measurement of the outer seal edge (FIG. 16B). After all of these inner and outer seal edge measurements are obtained, they can be sorted to remove any spurious or out-of-range measurements which correspond to edges beyond the actual seal edge. The reason for this is that the geometry of the seal edge is sometimes discontinuous because of package variances, seal process variances and other process factors. A "best circle fit" algorithm may be used on the inner and outer seal edge measurements and a maximum variance defined for each to allow non-conforming measurement to be discarded. A subsequent "qualified best circle fit" of the edges will yield the most accurate possible measurements of seal edge position, roundness and concentricity.

It is important to position the seal area as flat as possible during the inspection process to obtain reliable measurement data of the seal's surface boundaries. Any variation in relative flatness will tend to cause the appearance of reflection "shadows" within the seal area edge which do not correspond to the actual seal boundary. In addition, variations in the part presentation to the camera 10 and variations in the illumination source must be minimized to prevent the appearance of ambiguous features.

In one application, the inventor has proposed a 4-inch aperture co-axial light source 2 being located at least 12 inches away from the outer boundaries of the heat seal area (±arctan 2/12) with a 105 mm lens located at a distance of 35 inches. In this case, a lighting distance of at least 18 inches is necessary to cause the art work 122 to be adequately suppressed by the "Inverse Square Law". The predicted optimum lighting solution is then a light source at a distance of 18 inches with an angular dimension (±arctan 2/18).

The present inventor has determined that there are five factors which must be taken into consideration, when designing an imaging system according to the present invention, to provide sufficient contrast of a desire feature. The first factor is the relative specularity of the specular areas and the diffuse areas. Second factor is the sensitivity of the imaging camera and the other associated imaging process hardware. The third factor is the sensitivity of the software which is used to interpret the sensed image derived by the observation device. The more sensitive the hardware and the software, the closer the observation device and illumination device can be placed to the object to be observed and conversely the less sensitive the hardware and software, the further the observation device and illumination device have to be placed from the object to be observed. The fourth factor is the effect of the "Inverse Square Law" by which the intensity of a diffuse reflection, back along the observation axis, will decrease proportionally with distance the further the observation device and the light source are placed along away from the object to be observed. Accordingly, the imaging device and the light source should be placed at a sufficient distance from the object to be observed so that the "Inverse Square Law" effect can be sensed by the imaging device. The fifth factor is the surface geometry of the object to be observed. The object should be flat or slightly concave or convex, e.g. the concave or convex contour of the surface to be observed should deviate no more that about a 10% from a perfectly planar surface.

The imaging device, according to the present invention, can be arranged to send a signal to the central processor 96 of the cigarette manufacturing device 60 to automatically shut down the device when the imaging device determines that a plurality sequentially arranged segments S of the cigarette paper 63 are defective, e.g. five sequentially arranged segments S are imaged as being defective. Such a continuous sequence of defective segments S would tend to indicate a more substantial production problem. It is also to be appreciated that the width, the number and the location of the strips of glue, applied to the cigarette paper 63, can vary from application to application.

In a preferred form of the invention, the imaging device is spaced from the object to be observed by a distance of about four, or even five or more, times the height H of the housing 18 (FIG. 14) containing the source of incident light. This spacing of the imaging device from the object to be observed facilitates proper perception of 100 percent of surface area located within the region of interest ROI and processing of the reflected light so that the imaging device is able to readily discern the specular areas from the diffuse areas.

Since certain changes may be made in the above described illumination device without departing from the spirit and scope of the invention herein involved, it is intended that all matter contained in the above description or shown in the accompanying drawings shall be interpreted merely as examples illustrating the inventive concept herein and shall not be construed as limiting the invention.

What is claimed is:

1. An imaging system with a desired field of view, for imaging a desired generally planar surface of an object, being located within said field of view, having a first area with specular reflection characteristics and a second area with diffuse reflection characteristics which are different from said specular reflection characteristics, said imaging system comprising:

a source of incident light, for supplying continuous co-axial diffuse light along an observation axis, to said desired surface of said object to be observed which is located within said field of view whereby the entire desired generally planar surface to be observed, including both said first and second areas, is supplied with said co-axial diffuse light, and said first area, having said specular reflection characteristics, reflecting a substantial portion of said supplied co-axial diffuse light back, along said observation axis while said second area, having said diffuse reflection characteristics, scattering said supplied co-axial diffuse light in a variety of different reflection directions so that at least a portion of said supplied co-axial diffuse light is reflected back along said observation axis;

an imaging device for receiving the reflected light representing an optical image of said surface of said object to be observed, said imaging device being located along said observation axis and being spaced a sufficient distance from said surface of said object so that said imaging device is able to perceive a reflection from the entire desired generally planar surface to be observed as well as detect a difference in reflection intensity between said first area and said second area and process said reflection of at least said first area, having said specular reflection characteristics, as being relatively bright, while perceiving said reflection of at least said second area, having said diffuse reflection characteristics, as being relatively dark, in comparison to said first area, for discerning a characteristic of at least one of said first and said second areas; and said specular reflection is provided by a length of cigarette paper and said diffuse reflection is provided by glue, and said imaging system, based upon said reflected optical image, determines a location of said glue relative to said length of cigarette paper.

2. An imaging system according to claim 1, further including a light barrier encasing said observation axis and extends from said source of incident light to a location adjacent said surface of said object to be observed, to prevent surrounding environmental light from affecting the imaging of the object to be observed by said imaging system.

3. An imaging system according to claim 1, wherein said source of incident light comprises:
 a light source for casting light at a beam splitter, positioned along said observation axis;
 a light trap, located remote from said light source, for absorbing unreflected light passing through said beam splitter; and
 a diffuser is positioned between said light source and said beam splitter for diffusing the light supplied by said light source.

4. An imaging system according to claim 1, wherein said characteristic of at least one of said first and said second areas discerned by said imaging device is one of the location of a boundary between said first and said second areas, the presence of a boundary between said first and said second areas, the absence of a boundary between said first and said second areas, the orientation of one of said first and said second areas, the shape of one of said first and said second areas and the location of one of said first area relative to said second area.

5. An imaging system according to claim 1, wherein said specular reflection is provided by a first material and said diffuse reflection is provided by a second material which is different from said first material, and said imaging system, based upon said reflected optical image, determines the location of said second material relative to said first material.

6. An imaging system according to claim 5, wherein said first material is a length of cigarette paper and said second material is glue applied to a surface of said cigarette paper to facilitate gluing of said cigarette paper into finished cigarette product, and said imaging system includes a processing system for discerning at least whether or not said glue is applied to said cigarette paper at a desired location.

7. An imaging system according to claim 1, wherein said source of incident light is housed within a housing having a height and said imaging device is spaced from said object to be observed, along said observation axis, by distance of at least four times the height of said housing.

8. An imaging system according to claim 7, wherein said housing includes first and second apertures and a beam splitter is located between said first and said second apertures.

9. An imaging system according to claim 1, wherein said source of incident light comprises one of bulbs, incandescent fiber optics, LEDs or fluorescent light.

10. An imaging system according to claim 1, wherein said source of incident light comprises:
 a light source for casting light at a curved beam splitter, positioned along said observation axis;
 a light trap, located remote from said light source, for absorbing unreflected light passing through said curved beam splitter; and
 a diffuser is positioned between said light source and said curved beam splitter for diffusing the light supplied by said light source, and said curved beam splitter facilitates collimation of the diffuse light toward said object to be observed.

11. An imaging system according to claim 1, wherein said imaging system further includes a computer, which is coupled to a manufacturing device, for controlling operation thereof, and said computer is coupled to said imaging device, and said imaging device, based upon the discerned characteristic of at least one of said first and said second areas, sends a signal to said computer for use by said computer in controlling the operation of said manufacturing device.

12. An imaging system according to claim 1, wherein said discerned characteristic of at least one of said first and said second areas is an inspection of said object to be observed to determine whether said object is one of acceptable or defective.

13. In a cigarette manufacturing device comprising a continuous roll of cigarette paper, a plurality of transfer rollers for conveying said cigarette paper through said cigarette manufacturing device, a glue application station for applying glue to only a portion of a surface of said cigarette paper, and a rolling station for rolling said cigarette paper, with a filter and pre-rolled tobacco components into a finished cigarette product;

the improvement wherein said cigarette manufacturing device is provided with an imaging system for imaging a surface of said cigarette paper following the application of glue thereto, said imaging system comprising a source of incident light for supplying co-axial diffuse light, along an observation axis, to said cigarette paper, following the application of glue thereto, whereby both a portion of said cigarette paper having glue and a portion of said cigarette paper remaining unglued are supplied with co-axial diffuse light, and said glued portion reflecting a substantial portion of the supplied co-axial diffuse light back along said observation axis while said unglued portion of said cigarette paper, having diffuse reflection characteristics, scatters the supplied co-axial diffuse light in a plurality of different reflective directions so that only a minor portion of the supplied co-axial diffuse light is reflected back along said observation axis;

an imaging device for receiving the reflected light representing an optical image of said cigarette paper, said imaging device being spaced a sufficient distance from said cigarette paper so that each said portion of said cigarette paper containing glue is perceived by said imaging device as being of a relatively bright intensity while each said portion of said cigarette paper which is unglued is perceived by said imaging device as being of a relatively dark intensity, in comparison to said glued portions, whereby the inspection of the application of glue to said cigarette paper is achieved.

14. A method of imaging a desired generally planar surface area of an object, being located within a field of view of an imaging system, having a first area with specular reflection characteristics and a second area with diffuse reflection characteristics which are different from said specular reflection characteristics, said method comprising the steps of:

supplying a source of incident light of continuous co-axial diffuse light, along an observation axis, to said desired surface area of said object to be observed which is located within said field of view whereby the entire desired surface area to be observed, including both said first and second areas, is supplied with said co-axial diffuse light;

reflecting a substantial portion of said supplied co-axial diffuse light back, via said first area having said specular reflection characteristics, along said observation axis;

scattering said supplied co-axial diffuse light in a variety of different reflection directions, via said second area having said diffuse reflection characteristics, so that only a portion of said supplied co-axial diffuse light is reflected back along said observation axis;

receiving the reflected light, representing an optical image of said surface of said object to be observed, with an imaging device; and locating said imaging device along said observation axis a sufficient distance from said surface of said object so that said imaging device is able to perceive a reflection from the entire desired surface area to be observed as well as detect a difference in reflection intensity between said first area and said second area and process said reflection of at least said first area, having said specular reflection characteristics, as being relatively bright while perceive said reflection of at least said second area, having said diffuse reflection characteristics, as being relatively dark, in comparison to said first area, for discerning a characteristic of at least one of said first and said second areas; and supplying said source of incident light through at least one aperture, provided in said source of incident light, and determining a size of said at least one aperture according to the formula:

Aperture Size=$(2P+A)-((P+A)(Z-LZ)/Z)$

Where:

A=an entrance pupil diameter of a lens of said imaging device;

P=a maximum width of said object to be observed;

Z=a distance between the lens and a top surface of said object to be observed, measured along said observation axis; and LZ=a distance from a too of a housing containing said source of incident light to the top of said object to be observed, measured along said observation axis.

15. An imaging system with a desired field of view, for imaging a desired generally planar surface of an object, being located within said field of view, having a first area with specular reflection characteristics and a second area with diffuse reflection characteristics which are different from said specular reflection characteristics, said imaging system comprising:

a source of incident light, for supplying continuous co-axial diffuse light along an observation axis, to said desired surface of said object to be observed which is located within said field of view whereby the entire desired generally planar surface to be observed, including both said first and second areas, is supplied with said co-axial diffuse light, and said first area, having said specular reflection characteristics, reflecting a substantial portion of said supplied co-axial diffuse light back along said observation axis while said second area, having said diffuse reflection characteristics, scattering said supplied co-axial diffuse light in a variety of different reflection directions so that at least a portion of said supplied co-axial diffuse light is reflected back along said observation axis;

an imaging device for receiving the reflected light representing an optical image of said surface of said object to be observed, said imaging device being located along said observation axis and being spaced a sufficient distance from said surface of said object so that said imaging device is able to perceive a reflection from the entire desired generally planar surface to be observed as well as detect a difference in reflection intensity between said first area and said second area and process said reflection of at least said first area, having said specular reflection characteristics, as being relatively bright, while perceiving said reflection of at least said second area, having said diffuse reflection characteristics, as being relatively dark, in comparison to said first area, for discerning a characteristic of at least one of said first and said second areas; and said source of incident light is supplied through at least one aperture, provided in said source of incident light, and said at least one aperture has a size which is determined according to the formula:

Aperture Size=$(2P+A)-((P+A)(Z-LZ)/Z))$

Where:

A=an entrance pupil diameter of a lens of said imaging device;

P=a maximum width of said object to be observed;

Z=a distance between the lens and a top surface of said object to be observed, measured along said observation axis; and LZ=a distance from a top of a housing containing said source of incident light to the top of said object to be observed, measured along said observation axis.

16. An imaging system with a desired field of view, for imaging a desired generally planar surface of an object, being located within said field of view, having a first area with specular reflection characteristics and a second area with diffuse reflection characteristics which are different from said specular reflection characteristics, said imaging system comprising:

a source of incident light, for supplying continuous co-axial diffuse light along an observation axis, to said desired surface of said object to be observed which is located within said field of view whereby the entire desired generally planar surface to be observed, including both said first and second areas, is supplied with said co-axial diffuse light, and said first area, having said specular reflection characteristics, reflecting a substantial portion of said supplied co-axial diffuse light back along said observation axis while said second area, having said diffuse reflection characteristics, scattering said supplied co-axial diffuse light in a variety of different reflection directions so that at least a portion of said supplied co-axial diffuse light is reflected back along said observation axis;

an imaging device for receiving the reflected light representing an optical image of said surface of said object to be observed, said imaging device being located along said observation axis and being spaced a sufficient distance from said surface of said object so that said imaging device is able to perceive a reflection from the entire desired generally planar surface to be observed as well as detect a difference in reflection intensity between said first area and said second area and process said reflection of at least said first area, having said specular reflection characteristics, as being relatively bright, while perceiving said reflection of at least said second area, having said diffuse reflection characteristics, as being relatively dark, in comparison to said first area, for discerning a characteristic of at least one of said first and said second areas; and a light barrier encasing said observation axis and extending from said source of incident light to a location adjacent said surface of said object to be observed, to prevent surrounding environmental light from affecting the imaging of the object to be observed by said imaging system; and an inwardly facing surface of said barrier being provided with a light absorbing material to absorb light contacting said inwardly facing surface of said barrier.

17. An imaging system according to claim 16, wherein said source of incident light is supplied through at least one aperture, provided in said source of incident light, and said at least one aperture has a size which is determined according to the formula:

$$\text{Aperture Size} = (2P+A) - ((P+A)(Z-LZ)/Z)$$

Where:

A = an entrance pupil diameter of a lens of said imaging device;

P = a maximum width of said object to be observed;

Z = a distance between the lens and a top surface of said object to be observed, measured along said observation axis; and LZ = a distance from a top of a housing containing said source of incident light to the top of said object to be observed, measured along said observation axis.

18. An imaging system according to claim 16, wherein a piece of glass seals a base of said light barrier located adjacent to surface of said object to be observed.

* * * * *